US008058505B2

(12) United States Patent
Horiuchi

(10) Patent No.: US 8,058,505 B2
(45) Date of Patent: Nov. 15, 2011

(54) **CYBRID PLANT OF THE GENUS *LACTUCA* AND METHOD FOR PRODUCING THE SAME**

(75) Inventor: Shingo Horiuchi, Kanagawa (JP)

(73) Assignee: Sakata Seed Corporation, Yokohama-Shi (JP)

( * ) Notice: Subject to any disclaimer, the term of this patent is extended or adjusted under 35 U.S.C. 154(b) by 552 days.

(21) Appl. No.: 12/084,067

(22) PCT Filed: Oct. 20, 2006

(86) PCT No.: PCT/JP2006/321456
§ 371 (c)(1),
(2), (4) Date: Apr. 24, 2008

(87) PCT Pub. No.: WO2007/049730
PCT Pub. Date: May 3, 2007

(65) Prior Publication Data
US 2010/0077499 A1    Mar. 25, 2010

(30) Foreign Application Priority Data

Oct. 26, 2005  (JP) .................. 2005-311598

(51) Int. Cl.
*A01H 5/00* (2006.01)
*A01H 1/00* (2006.01)
*C12N 15/05* (2006.01)
*C12N 15/08* (2006.01)
(52) U.S. Cl. ........ 800/277; 800/304; 800/305; 435/440; 435/449; 435/463; 435/419; 435/421; 435/428; 435/430
(58) Field of Classification Search .................. None
See application file for complete search history.

(56) References Cited

U.S. PATENT DOCUMENTS

| 5,254,802 A | 10/1993 | Hoekstra et al. |
| 5,360,725 A * | 11/1994 | Akagi et al. .................. 435/453 |
| 5,650,559 A | 7/1997 | Akamatsu et al. |
| 5,789,566 A | 8/1998 | Bonhomme et al. |
| 5,866,782 A | 2/1999 | Iwabuchi et al. |
| 6,803,497 B1 | 10/2004 | Delesalle et al. |

FOREIGN PATENT DOCUMENTS

| EP | 214601 A2 | 3/1987 |
| EP | 0 327 970 A2 | 8/1989 |
| EP | 0363819 A1 | 4/1990 |
| EP | 0675198 A1 | 10/1995 |
| EP | 771523 A1 | 5/1997 |
| EP | 0771523 B1 | 5/1997 |
| EP | 0810284 A1 | 12/1997 |
| JP | 62-65631 A | 3/1987 |
| JP | 62-232324 A | 10/1987 |
| JP | 63-36776 A | 2/1988 |
| JP | 63-79548 A | 4/1988 |
| JP | 64-20041 A | 1/1989 |
| JP | 1-196239 A | 8/1989 |
| JP | 1-206931 A | 8/1989 |
| JP | 1-218530 A | 8/1989 |
| JP | 2-138927 A | 5/1990 |
| JP | 2-303426 A | 12/1990 |
| JP | 7-31307 A | 2/1995 |
| JP | 10-52185 A | 2/1998 |
| JP | 10-108676 A | 4/1998 |
| JP | 10-108677 A | 4/1998 |
| JP | 2001-145497 A | 5/2001 |
| JP | 2002-512050 T | 4/2002 |
| JP | 2002-247927 A | 9/2002 |
| JP | 3635036 B2 | 1/2005 |
| JP | 2005-110623 A | 4/2005 |
| WO | WO 95/09910 A1 | 4/1995 |
| WO | WO 97/09873 A1 | 3/1997 |
| WO | WO 97/45548 A1 | 12/1997 |
| WO | WO 99/55143 A1 | 11/1999 |

OTHER PUBLICATIONS

Reiseberg et al, The Journal of Heredity, vol. 85, No. 3, pp. 233-238, 1994.*
GenEmbl Accession No. X62592.*
GenEmbl Accession No. X53537.*
GenEmbl Accession No. X55963.*
Curtis et al., "Genomic Male Sterility in Lettuce, A Baseline for the Production of F-1 Hybrids", Plant Science, vol. 113, No. 1, (1996) pp. 113-119.
European Search Report issued in EP patent application No. 06822425.2 on Feb. 1, 2010.
Nakano et al., "Plant Regeneration from Protoplasts of Gentiana by Embedding Protoplasts in Gellan Gum", Plant Cell Tissue and Organ Culture, vol. 41, No. 3, (1995) pp. 221-227.
Nishio et al., "Simple and Efficient Protoplast Culture Procedure of Lettuce *Lactuca-sativa* L", Japanese Journal of Breeding, vol. 38, No. 2, (1988) pp. 165-171.
Rambaud et al., "Male-sterile Chicory Cybrids Obtained by Intergeneric Protoplast Fusion", Theoretical and Applied Genetics, vol. 87, No. 1, (1993) pp. 347-352.
Varotto et al., "Production of asymmetric somatic hybrid plants between *Cichorium intybus* L. and *Helianthus annuus* L.", Theor. Appl. Genet., vol. 102, No. 6/7, (2001) pp. 950-956.
Bond, "A Short Review of Research on Male Sterility and Prospects for F1 Hybrid Varieties in Field Beans (*Vicia faba* L.)", Euphytica, vol. 41, 1989, pp. 87-90, Kluwer Academic Publishers, Dordrecht, the Netherlands.
Dubreucq et al., "Analyses of Mitochondrial DNA Structure and Expression in Three Cytoplasmic Male-Sterile Chicories Originating from Somatic Hybridisation Between Fertile Chicory and CMS Sunflower Protoplasts", Theor. Appl. Genet., vol. 99, 1999, pp. 1094-1105.
Horn, "A Microchondrial 16 kDa Protein is Associated With Cytoplasmic Male Stertility in Sunflower", Plant Molecular Biology, vol. 17, 1991, pp. 29-36, Kluwer Academic Publishers, Belgium.

(Continued)

*Primary Examiner* — Eileen B O'Hara
(74) *Attorney, Agent, or Firm* — Birch, Stewart, Kolasch & Birch, LLP

(57) ABSTRACT

A cytoplasmic male sterile cybrid plant of the genus *Lactuca*, a progeny thereof, or a part thereof having a gene derived from the mitochondria of a plant of the genus *Helianthus* in its cytoplasm and methods of producing first filial generation seeds using such a cybrid plant.

14 Claims, 16 Drawing Sheets

OTHER PUBLICATIONS

Horn, "Molecular Diversity of Male Sterility Inducing and Male-Fertile Cytoplasms in the Genus *Helianthus*", Theor. Appl. Genet., vol. 104, 2002, pp. 562-570.

Matsumoto, "Interspecific Somatic Hybridization Between Lettuce (*Lactuca sativa*) and Wild Species *L. virosa*", Plant Cell Reports, vol. 9, 1991, No. 10, pp. 531-534.

Mizutani et al., "Plant Regeneration and Cell Fusion of Protoplasts from Lettuce Cultivars and Related Wild Species in Japan", Bull. Fac. Agr., Saga Univ., vol. 67, 1989, pp. 109-118.

Rambaud et al., "Molecular Analysis of the Fourth Progeny of Plants Derived From a Cytoplasmic Male Sterile Chicory Cybrid", Plant Breeding, vol. 116, 1997, pp. 481-486.

Ryder et al., "A Recessive Male Sterility Gene in Lettuce (*Lactuca sativa* L)", Proceedings of the American Society for Horticultural Science, vol. 91, 1967, pp. 366-368 (with photo page).

Ryder et al., "An Epistatically Controlled Pollen Sterile in Lettuce (*Lactuca sativa* L)", Proceedings of the American Society for Horticultural Science, vol. 83, 1963, pp. 585-589 (with photo page).

Ryder, "Studies of Three New Genes, Linkage, and Epistasis in Lettuce", Journal for the American Horticultural Society, vol. 114, No. 1, Jan. 1989, pp. 129-133 (with cover page).

Serizawa, "Recessive Male Sterile Gene in Lettuce (in Japanese)", Journal of Japanese Society for Horticultural Science, vol. 73, Supl. 2, p. 556, with English translation.

Sukno et al., "Interspecific Hybridization Between Sunflower and Wild Perennial Helianthus Species Via Embryo Rescue", Euphytica, vol. 106, 1999, pp. 69-78 (with cover page), Kluwer Academic Publishers, the Netherlands.

Takada et al., "Study on F1 Seed Production in Lettuce (1): Heterosis of F1 Plants Using Male Sterile Lines as Seed Parents (in Japanese)", 1987 Spring Conference of Japanese Society for Horticultural Science, Research Abstract 208-209.

Takada, "Development of Techniques Using Male Sterility in Lettuce (1): Expresion of Heterosis in F1 Hybrids (in Japanese)", National Institute of Vegetable and Tea Science, Morioka Research Station, Annual Research Report No. 1, 1986, pp. 87-93.

Variety Registration Application "Fine" (in Japanese), Kaneko Seeds, No. 1745, Partial Translation.

Horn et al., "Fertility Restoration of New CMS Sources in Sunflower (Helianthus annuus L.)", Plant Breeding, vol. 116, No. 4, Sep. 1997, pp. 317-322.

\* cited by examiner

Figure 1
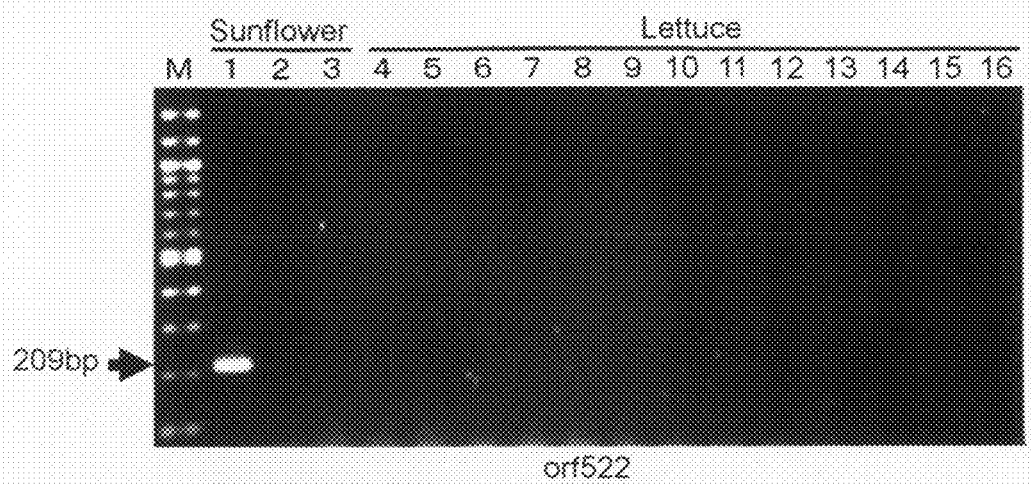
orf522
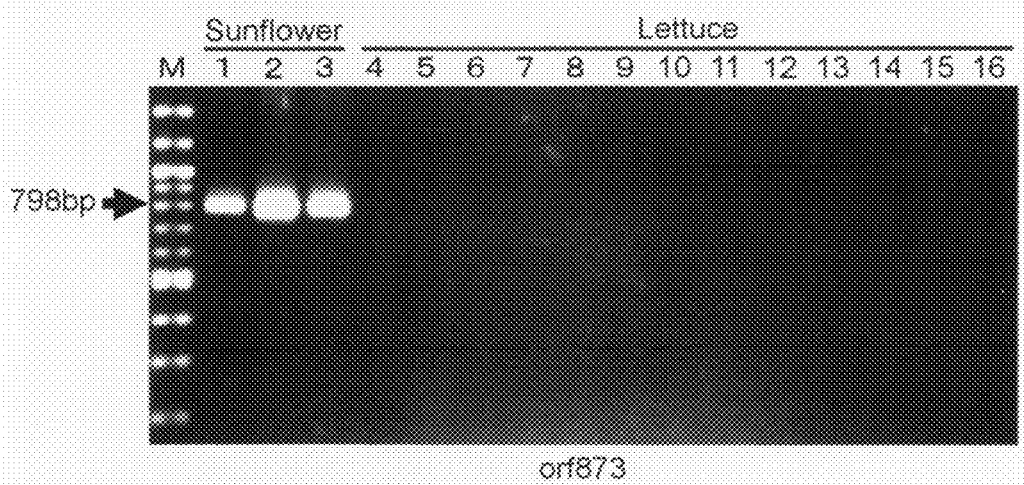
orf873

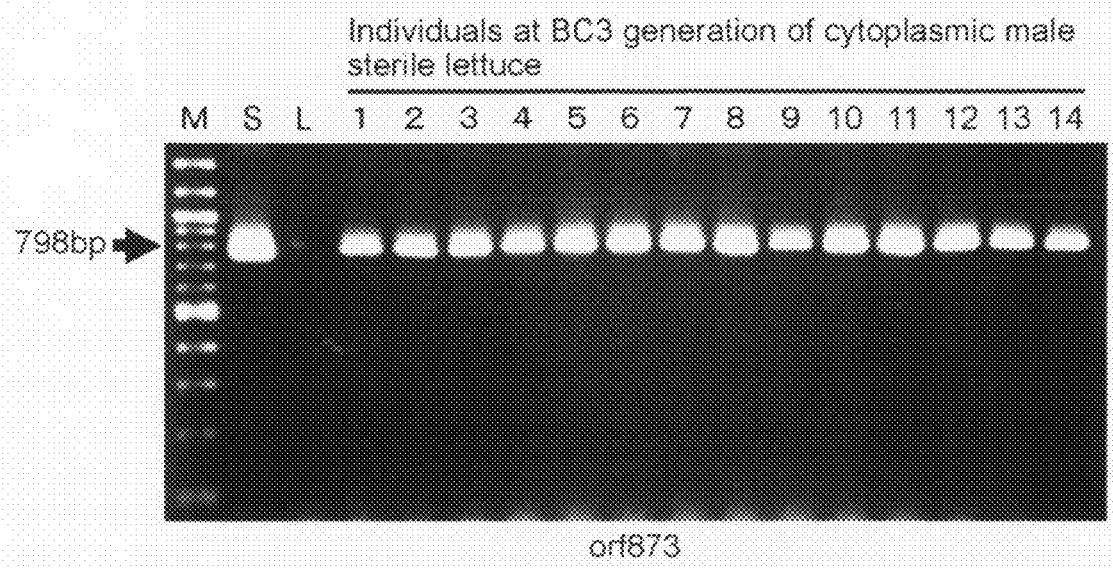

Figure 9A
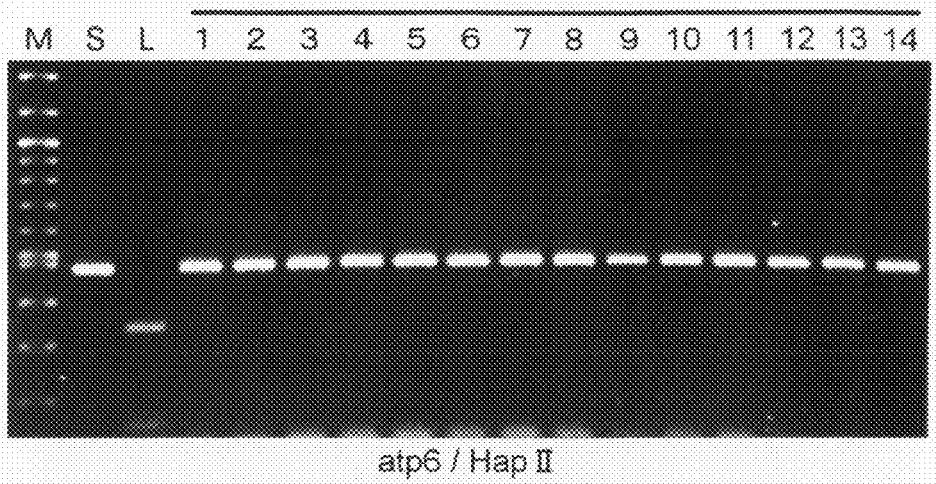
atp6 / Hap II
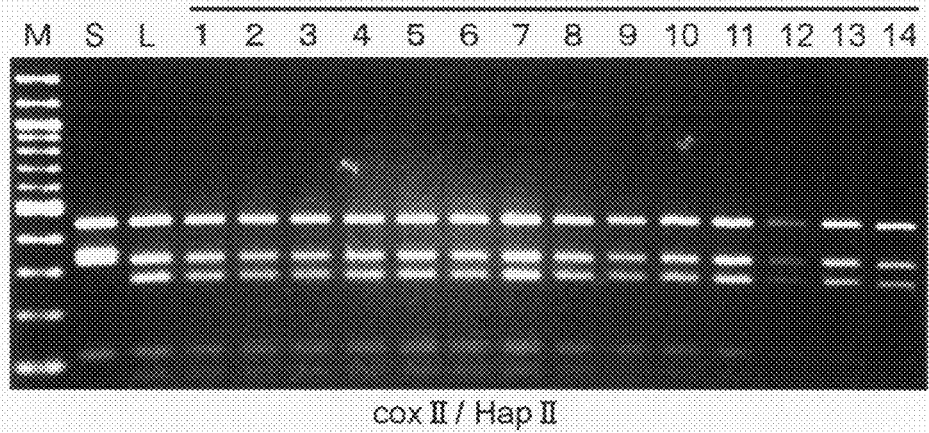
cox II / Hap II
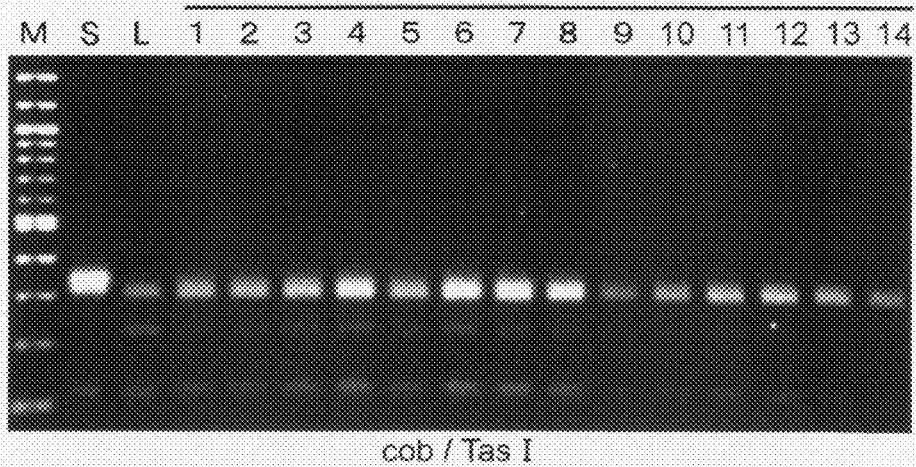
cob / Tas I

Figure 9B
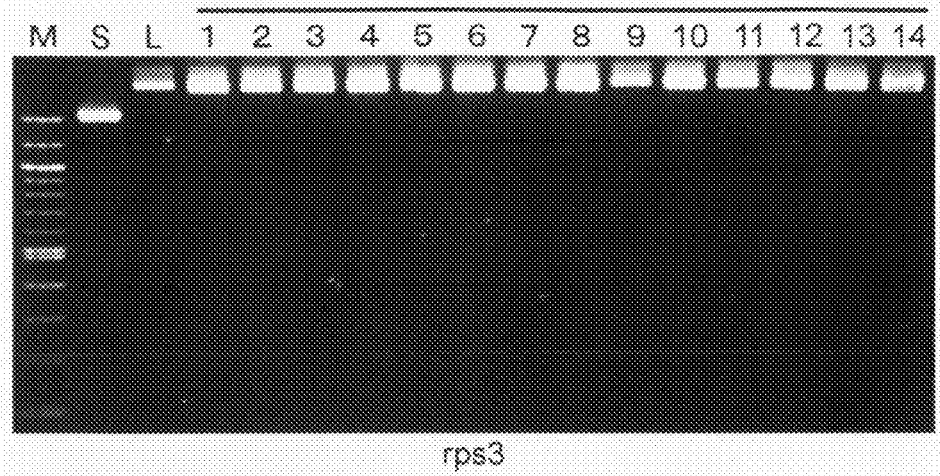
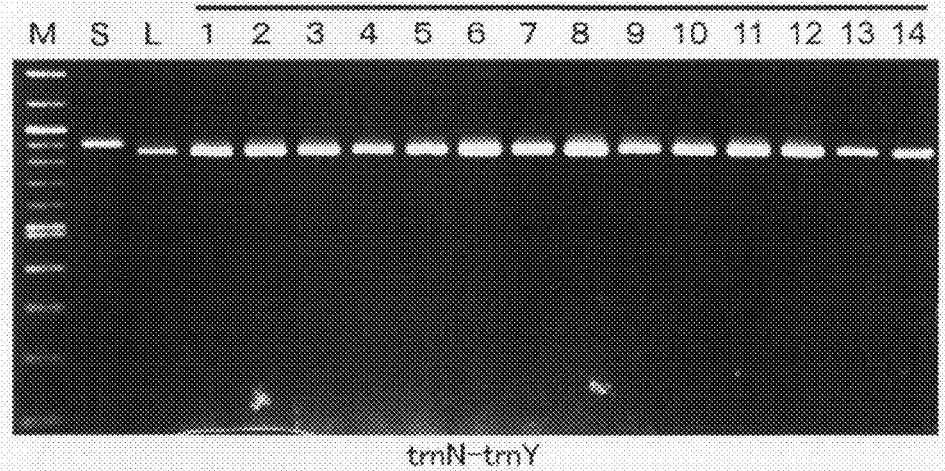
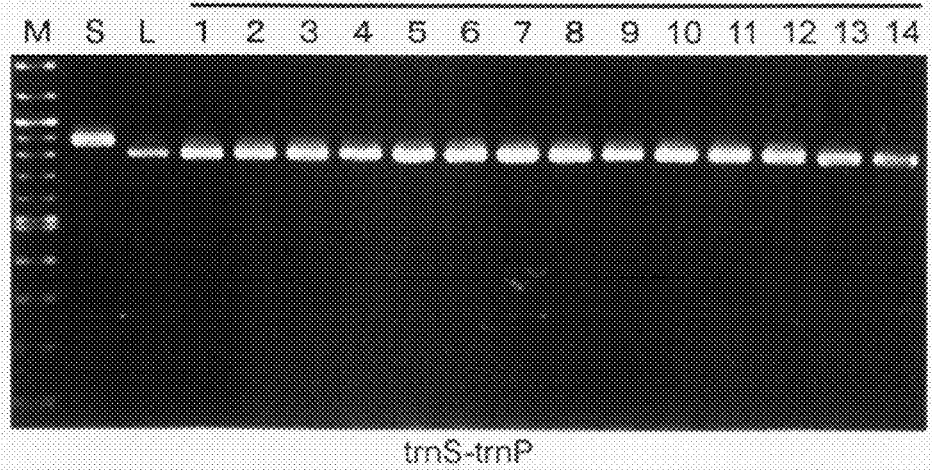

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
cgtccttgcg tgagggtttg                                            20

<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
tgagtaccgt tctctcacga gttg                                       24

<210> SEQ ID NO 3
<211> LENGTH: 24

```
<212> TYPE: DNA
<213> ORGANISM: Artificial Sequence
<220> FEATURE:
<223> OTHER INFORMATION: Synthetic primer

<400> SEQUENCE: 3
gctactcgga cgaaaactag gaac                                          24

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cccaacttca cgcggaacag                                               20

<210> SEQ ID NO 5
<211> LENGTH: 23
<212> TYPE: DNA
<213> ORGANISM: Artificial Sequence
<220> FEATURE:
<223> OTHER INFORMATION: Synthetic primer

<400> SEQUENCE: 5
tcaacctgga gttccgcctg aag                                           23

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
gtgccctaaa gttcctccac cgaa                                          24

<210> SEQ ID NO 7
<211> LENGTH: 23
<212> TYPE: DNA
<213> ORGANISM: Artificial Sequence
<220> FEATURE:
<223> OTHER INFORMATION: Synthetic primer

<400> SEQUENCE: 7
gctaactctc agtttggtcc tac                                           23

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ccagaccggt taatgcaaga                                               20

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
ctggcttacc ggtaatctcc aa                                            22
```

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
cttgcaagtt tccccgcaaa                                              20

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
tcttctccac actgaatcag ca                                           22

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
agaatgggcg ttatggcaaa g                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ggaaatccga tttcggtaag                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
agggtccttt taagtggatg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gagcggtcgg ctgttaactg                                              20

<210> SEQ ID NO 16
<211> LENGTH: 27
<212> TYPE: DNA
<213> ORGANISM: Artificial Sequence
<220> FEATURE:
<223> OTHER INFORMATION: Synthetic primer

```
<400> SEQUENCE: 16
cagatttaca gtctgtcgct tttaacc                                        27

<210> SEQ ID NO 17
<211> LENGTH: 26
<212> TYPE: DNA
<213> ORGANISM: Artificial Sequence
<220> FEATURE:
<223> OTHER INFORMATION: Synthetic primer

<400> SEQUENCE: 17
ggcattggtt tgctaaatcg acatac                                         26

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
acctatggcc ctctgtaccc                                                20
```

CYBRID PLANT OF THE GENUS *LACTUCA* AND METHOD FOR PRODUCING THE SAME

This application is a National Stage Application under 35 U.S.C. §371(c) of PCT Application No. PCT/JP2006/321456, filed Oct. 20, 2006, and published Mar. 5, 2007, as WO 2007/049730 A1, which claims the priority of Japanese Patent Application No. 2005-311598 filed Oct. 26, 2005. The entire disclosure and contents of the above applications are hereby incorporated by reference herein.

TECHNICAL FIELD

The present invention relates to a cybrid plant of the genus *Lactuca* and a method for producing the same.

BACKGROUND ART

Conventionally, true breeding and first filial generation (hereinafter referred to as F1) varieties have been generated as plant varieties. Among them, F1 varieties have become popular for staple crops. F1 varieties have major advantages including high growth rates, high yields, etc., as a result of high growing vigor due to hybrid vigor (heterosis). Additionally, they may be expected to have improvements in resistance to diseases and pest insects, and/or in adaptability to the environment, such as cold and heat resistance. Moreover, plants of an F1 variety have the same genotype, while they are heterozygous, and show very high uniformity in their phenotypes, increasing marketability of products from them. Furthermore, F1 varieties have increased probability of accumulating favorable traits that are governed by a dominant gene(s), enabling rapid breeding. Also, they provide a major advantage of protecting breeder's rights by raising the necessity of producing F1 seed every year for seed production, as their progeny will loose the uniformity in quality from the next generation as a result of segregation of the traits.

F1 varieties have become mainstream cultivated varieties for staple crops for the aforementioned reasons. For large scale production of F1 seed for commercial purposes, however, an economical and non-laborious method for emasculation is required. For plants that allow production of many seeds upon a single cross, including vegetables such as tomato, melon, cucumber and pumpkin, and flowering plants such as petunia and eustoma, economical production of F1 seed can be achieved by manual emasculation and crossing. However, there are still many crops that are very difficult to emasculate efficiently because of their flower structures. Crops that produce only a little amount of seed upon a single cross are difficult to produce hybrid seed in large quantities by manual crossing, making the production of F1 seed uneconomical. For seed production of such crops, it is crucial to develop a method using male sterility for seed production, because the laborious and expensive process of emasculation can be omitted by employing a male sterile plant as a seed parent, thus taking advantage of the genetic characteristics of male sterility.

Male sterility has been found in many plant species. And, methods for producing male sterile plants using protoplast fusion techniques have been established in many useful crops (Patent Documents 4, 5, 6, 7, 8, 9, 10, 11, 12, 13, 14, 15, 16, 17, 18, and 19). There are various mechanisms for male sterility, which may be classified into two categories, the genetic male sterility and the cytoplasmic male sterility. Genetic male sterility is caused by a nuclear gene(s). On the other hand, cytoplasmic male sterility involves the interaction between a cytoplasmic genetic factor(s) and a nuclear gene(s).

Lettuce is produced in every country in the world. It is a vegetable of a very large market size, and the creation of its F1 varieties is highly desired. Non-patent Documents 1 and 2 describe the expression of heterosis in lettuce. The expression of heterosis is investigated by comparing F1 plants produced by using a genetic male sterile lettuce with conventional true breeds. At the conclusion of the investigation the investigators reported that the F1 plants exhibited outstanding heterosis. Consequently, a strong demand has been raised to establish a seed production technique using male sterility of lettuce to produce F1 seed efficiently. Yet such technique has not been established. For example, although Non-patent Document 3 revealed the mode of inheritance of genetic male sterility in lettuce, the practical application of genetic male sterility has remained problematic as it is unstable in male sterility and even female fertility appears to be defective (Non-patent Document 7). The author of Non-patent Document 3 also reported similar results in Non-patent Documents 4 and 5. Actually, while an F1 variety created by using genetic male sterility has been brought to market, it is unstable in male sterility and remains unable to replace the conventional true breed (Non-patent Document 6).

More recently, a novel type of genetic male sterile lines has been found. For example, the line "MS1024" described in Patent Document 1 and Non-patent Document 1 was found among progeny of plants selected for disease resistance. The line is superior to the genetic male sterile plants described in Non-patent Document 3 and the like in that it produces no pollen grain at all in its male sterility and that it provides a higher yield of seed.

However, the commercial F1 seed production using genetic male sterile plants still has a problem in the production cost. In lettuce, genetic male sterility results from homozygosis for a recessive gene in the cases observed so far (Non-patent Document 7). Because the male sterile plants resulted from homozygosis for a recessive gene are not able to reproduce by themselves, in order to maintain and reproduce a male sterile line it is necessary to cross them with individuals that are heterozygous for the male sterile gene, and screen their progeny for the individuals that are homozygous for the male sterile gene. Because the cross will result in 1:1 phenotypic segregation into fertile plant individuals and sterile plant individuals, about 50% of the hybrid progeny will be male sterile plant individuals. Therefore, for commercial F1 seed production the plants in seed farms must be screened to find and remove the fertile plant individuals in some way. In the case of lettuce this removing process is especially troublesome because it has small flower organs, making it difficult to distinguish sterile plant individuals and fertile plant individuals, and it produces many flowers on slender flower stalks.

Furthermore, the blooming stage is different for each individual so it is very laborious to remove fertile individuals completely based on the appearance of flowers, and the purity of F1 seed may be lowered by errors in the removing process, which may cause a problem by reducing the seed quality.

Additionally, breeding of genetic male sterile plants is inefficient and requires a long period of time because the individuals with the male sterile gene are visually indistinguishable from others except at the blooming stage. To facilitate the distinction between fertile plants and sterile plants, it is necessary to develop a method to select only the male sterile plants either by finding and making use of a gene that is linked to the morphology of seed in an early stage of growth, or by developing a DNA marker that is linked to the male sterile gene. Such a technique has not yet been established for lettuce, although studies for that are still under way.

Although it has been a long time since the mode of inheritance of genetic male sterility in lettuce was revealed, many problems in the development of F1 varieties using a genetic male sterile lettuce still remain unsolved as described above, and the creation of F1 varieties with high marketability is still difficult.

On the other hand, the production of F1 seed using cytoplasmic male sterility has been in practical use for a long time in sunflower, sugar beet, potato, rice, wheat, carrot, onion, and allium, etc., and commercial production systems for those crops have been established. Also in cole crops such as cabbage, broccoli, radish, and Chinese cabbage, in which F1 seed production using self-incompatibility has been widely used, use of cytoplasmic male sterility for F1 seed production has become popular recently due to the demand for seed of higher quality.

In general, once a cytoplasmic male sterile plant with stable male sterility is produced, cytoplasmic male sterility can be introduced into many desirable lines by repeated backcrossing and breeding of seed parents for F1 varieties becomes possible. Because cytoplasmic male sterility is transmitted by cytoplasmic inheritance, the progeny will be all male sterile. Cytoplasmic male sterile lines can be maintained and proliferated easily by crossing with a maintainer line that has the same nuclear genome and normal cytoplasm. Since there is no need of removing fertile individuals from seed parents in seed farms as in the seed production using genetic male sterility mentioned above, the seed production using cytoplasmic male sterility is efficient, and without the problem of the decreased purity of F1 seed due to errors in the removing process.

Based on these facts, a method for F1 seed production using a cytoplasmic male sterile plant is expected to be much more useful in an economical and commercial sense compared to those using genetic male sterility.

Despite the expectation that such a method would be highly useful as described above, a method for F1 seed production using a cytoplasmic male sterile plant in lettuce has not yet been developed. This is because, for lettuce, there is no crossable plant of the same species or genus that has cytoplasm with the ability to cause cytoplasmic male sterility when introduced into the cytoplasm of lettuce.

On the other hand, for sunflower cultivated species (*Helianthus annuus* L.) of the genus *Helianthus* of the family Asteraceae, many cytoplasmic male sterile plants have been found from the interspecific hybridization and F1 varieties are in practical use. Non-patent Documents 9-13 and other documents have reported on these. As an example of the production of a cytoplasmic male sterile vegetable in the family Asteraceae, it is known that cytoplasmic male sterile chicory can be produced by protoplast fusion of sunflower and chicory. Such techniques are disclosed, for example, in Patent Documents 2 and 3, and Non-patent Documents 14 to 17.

Non-patent document 14 was the first report of the production of cytoplasmic male sterile chicory, and revealed that cytoplasmic male sterile chicory can be produced by introducing cytoplasm of sunflower into chicory using the protoplast fusion technique. Non-patent documents 14 reported also that the mitochondria genome in the produced cytoplasmic male sterile chicory resulted from the recombination of the mitochondria genomes of chicory and sunflower. Furthermore, Non-patent Documents 16 and 17 reported the results of the analyses on the expression of cytoplasmic male sterility and on mitochondrial DNA structure in the progeny of the aforementioned cytoplasmic male sterile chicory.

Patent Document 2 describes a cytoplasmic male sterile plant of the family Asteraceae and a method for obtaining such a plant. The only cytoplasmic male sterile plant that was shown to be actually produced in Patent Document 2 is cytoplasmic male sterile chicory as in Non-patent Document. 14. Although Patent Document 2 refers to cytoplasmic male sterile lettuce, it only states methods for culturing and fusing protoplasts with sentences in the present tense, and neither method nor experiment result of the actual production of cybrid lettuce or cytoplasmic male sterile lettuce has been described. In the protoplast fusion technique, the process is relatively easy until the step of isolating and fusing protoplasts. For example, it is even possible to isolate and fuse plant protoplasts and animal cells. However, the steps of culturing the fused cells between phylogenetically distant species to have them divide, and further regenerate a plant are technically very difficult. This is because of the increased technical difficulties due to the stress during the fusing process, which may suppress the cell division of the fused cells, and the genetic incompatibility between the nuclei and cytoplasm from heterologous origins. To overcome these difficulties to regenerate a plant, it is necessary to develop a method for fusing cells without hurting their cell membrane, and a culturing method that allows the fused cells with new genomic combinations to divide and regenerate into a plant. Therefore, the techniques of culturing fused cells and subsequently regenerating a plant from the fused cells are the core techniques of the protoplast fusion technique. Furthermore, for having the expression of male sterility, the recombination or rearrangement of the mitochondrial genomes between different species in an adequate phylogenetic distance is necessary to occur. Thus, even after it becomes possible to produce a cybrid plant from two distantly related species, it is not predictable if it will be possible to produce a plant that expresses male sterility, and therefore, the step of actually producing cybrid plants and selecting an individual that exhibits male sterility is essential. Thus, crucial techniques to produce cytoplasmic male sterile lettuce are not disclosed in Patent Document 2. For these reasons, even after Patent Document 2 there are no reports of the successful production of cytoplasmic male sterile lettuce despite that there has been a strong demand for developing a method for producing cytoplasmic male sterile lettuce for a long time.

Patent Document 3 discloses a method of producing cytoplasmic male sterile chicory by introducing orf522, a gene that is thought to be a causal gene for cytoplasmic male sterility in sunflower, into a plant of the genus *Cichorium* by asymmetric protoplast fusion.

Non-patent Document 15 describes the production of cytoplasmic male sterile chicory by a new research group, which, in recent years, has been conducting studies to produce cytoplasmic male sterile chicory suitable for practical use, in continuation of the work.

As described above, there are many reports of the production of cytoplasmic male sterile chicory by introducing a part of sunflower mitochondrial DNA by protoplast fusion. However, there are no reports of the production of cytoplasmic male sterile lettuce in spite that lettuce and chicory are both in the family Asteraceae. The difficulty of producing cytoplasmic male sterile lettuce using cytoplasmic male sterile sunflower may be due to low genetic compatibility between the lettuce nuclear genome and the sunflower mitochondrial genome, compared to the genetic compatibility between the chicory nuclear genome and the sunflower mitochondrial genome.

Furthermore, one may consider introducing cytoplasmic male sterility into lettuce by crossing it with cytoplasmic male sterile chicory that is produced by introducing the sunflower cytoplasmic male sterile gene into chicory. However sexual hybridization between lettuce and chicory is difficult because they are in different genera and distantly related. There are no known reports of the successful production of cytoplasmic male sterile lettuce using such a method.

As described above, the production of cytoplasmic male sterile lettuce is technically very difficult, and it has not been successful yet. However the creation of F1 varieties of lettuce using cytoplasmic male sterile lettuce will be very beneficial. Therefore, the creation of cytoplasmic male sterile lettuce has been highly desired.

Patent Document 1 Japanese Patent Laid-Open No. 2005-110623

Patent Document 2 European Patent No. 0771523

Patent Document 3 International Publication No. WO97/45548

Patent Document 4 Japanese Patent Laid-Open No. 62-232324

Patent Document 5 Japanese Patent Laid-Open No. 63-79548

Patent Document 6 Japanese Patent Laid-Open No. 02-303426

Patent Document 7 Japanese Patent Laid-Open No. 63-36776

Patent Document 8 Japanese Patent Laid-Open No. 64-20041

Patent Document 9 Japanese Patent Laid-Open No. 01-218530

Patent Document 10 Japanese Patent Laid-Open No. 10-052185

Patent Document 11 U.S. Pat. No. 5,254,802

Patent Document 12 Japanese Patent Laid-Open No. 10-108676

Patent Document 13 Japanese Patent Laid-Open No. 10-108677

Patent Document 14 Japanese Patent Laid-Open No. 2001-145497

Patent Document 15 Japanese Patent Laid-Open No. 02-138927

Patent Document 16 Japanese Patent Laid-Open No. 01-206931

Patent Document 17 International Publication No. WO99/55143

Patent Document 18 International Publication No. WO95/09910

Patent Document 19 International Publication No. WO97/09873

Patent Document 20 U.S. Pat. No. 3,635,036

Non-patent Document 1 Takada, Katuya and Fujino, Masatake (1987) "Study on F1 seed production in Lettuce (1): Heterosis of F1 plants using male sterile lines as seed parents (in Japanese)" 1987 Spring Conference of Japanese Society for Horticultural Science, Research Abstract 208-209.

Non-patent Document 2 Takada, Katuya and Fujino, Masatake (1986) "Development of techniques using male sterility in lettuce (1): Expression of heterosis in F1 hybrids (in Japanese)" National Institute of Vegetable and Tea Science, Morioka Research Station, Annual Research Report No. 1, 87-93.

Non-patent Document 3 Edwrd J. Ryder (1967) A recessive male sterility gene in Lettuce (*Lactica sativa L.*) Pro. Am. Soc. Hortic. Sci. 91, 366-368.

Non-patent Document 4 Ryder, E, J Proceeding of the American society for horticultural Science 1963 Vol. 83585-589 An epistatically controlled pollen sterile in Lettuce (*Lactica sativa L*).

Non-patent Document 5 Ryder, E, J Science 1989 vol. 114(1) 129-133 Studies of three new genes, linkage, and epistasis in Lettuce.

Non-patent Document 6 Variety Registration Application "Fine" (in Japanese), Kaneko Seeds, No. 1745.

Non-patent Document 7 Serizawa, Hiroaki, "Recessive male sterile gene in lettuce (in Japanese)" Journal of Japanese Society for Horticultural Science, vol. 73, Supl. 2, p. 566.

Non-patent Document 8 Matsumoto, E., Plant cell reports 1991. vol. 9(10) Interspecific somatic hybridization between lettuce (*Lactica sativa*) and wild species *L. virosa*

Non-patent Document 9 L. H. Rieseberg, C. Van Fossen, D. Arias, and R. L. Carter, The journal of heredity 1994: 85(3), 233-238 Cytoplasmic male sterility in Sunflower: origin, Inheritance, and Frequency in Natural Populations.

Non-patent Document 10 R. Horn Theor Appl Genet (2002) 104: 562-570 Molecular diversity of male sterility inducing and male-fertile cytoplasms in the genus *Helianthus*.

Non-patent Document 11 S. Sukno, J. Ruso, Euphytica (1999) 106: 69-78 Interspecific hybridization between sunflower and wild perennial *Herianthus* species via embryo rescue.

Non-patent Document 12 R. Horn, W. Friedt, Plant Breeding 116 (1997) 317-322 Fertility restoration of new CMS sources in sunflower (*Helianthus annuus L.*)

Non-patent Document 13 Horn, R., Plant molecular biology; an international journal on fundamental research and genetic engineering July 1991 v17(1), 29-36 A mitochondrial 16 kDa protein is associated with cytoplasmic male sterility in sunflower.

Non-patent Document 14 C. Rambaud, J. Dubois, J. Vasseur (1993) Male-sterile chicory cybrids obtained by intergeneric protoplast fusion, Theor Appl Genet 87: 347-352

Non-patent Document 15 S. Varotto, E. Nenz, M. Lucchin, P. Parrini (2001) Production of asymmetric somatic hybrid plants between *Cichorium intybus L.* and *Helianthus annuus L.*, Theor Appl Genet 102: 950-956.

Non-patent Document 16 C. Rambaud, A. Bellamy, A. Dubreucq, J.-C. Bourquin and J. Vasseur (1997) Molecular analysis of the fourth progeny of plants derived from a cytoplasmic male sterile chicory cybrid, Plant Breeding 116: 481-486

Non-patent Document 17 A. Dubreucq, Theor Appl Genet (1999): 1094-1105 Analyses of mitochondrial DNA structure and expression in three cytoplasmic male-sterile chicories originating from somatic hybridization between fertile chicoly and CMS sunflower protoplasts.

Non-patent Document 18 Mizutani, Takayuki (1989) "Plant regeneration and protoplast fusion using protoplasts of lettuce and related Japanese wild species (in Japanese)" Bull. Fac. Agr., Saga Univ 67: 109-118.

DISCLOSURE OF THE INVENTION

In view of the above problems in the conventional art, the present invention has an object to provide a cybrid lettuce of the genus *Lactuca* that is useful for F1 seed production of lettuce, and a method for producing the same.

The present inventors have diligently studied to solve the above problems and found that a stable cytoplasmic male sterile lettuce can be produced by using a method for culturing fused hybrid cells between sunflower and lettuce, and a method for regenerating a cybrid plant, and that F1 seed of lettuce can be produced efficiently by using this cytoplasmic male sterile lettuce, thereby completing the present invention.

Thus, the present invention encompasses the following inventions.

(1) A method for producing a cybrid plant of the genus *Lactuca*, characterized by comprising: fusing protoplasts from a plant of the genus *Helianthus* with protoplasts from a plant of the genus *Lactuca*; culturing one or more of the fused cells; and regenerating a plant from cells cultured from one or more of the fused cells.

(2) The method according to (1), wherein the protoplasts from a plant of the genus *Helianthus* are protoplasts from a plant of *H. annuus L.*, or protoplasts from a cytoplasm substitution line of *H. annuus L.* with cytoplasm from *H. petiolaris, H. argophyllus, H. debilis, H. decapetalus, H. giganteus, H. rigidus, H. salicifolius, H. anomalus, H. bolanderi, H. exilis, H. maximiliani, H. neglectus, H. praecox* or *H. tuberosus*.

(3) The method according to (1) or (2), wherein the protoplasts from a plant of the genus *Lactuca* are protoplasts from *Lactuca sativa L., L. serriola, L. aculeate, L. scarioloides, L. azerbaijanica, L. georgica, L. dregeana, L. altaica, L. saligna, L. virosa, L. tatarica, L. indica* or *L. debilis*, or an interspecific hybrid plant thereof.

(4) The method according to any one of (1) to (3), wherein the plant of the genus *Helianthus* is cytoplasmic male sterile.

(5) The method according to (4), wherein the plant of the genus *Helianthus* has a male sterile gene in mitochondria thereof.

(6) The method according to any one of (1) to (5), wherein the cybrid plant of the genus *Lactuca* is cytoplasmic male sterile.

(7) A cybrid plant of the genus *Lactuca* produced by the method according to any one of (1) to (6), or a progeny thereof, or a part thereof.

(8) The part of the cybrid plant of the genus *Lactuca* or the progeny thereof according to (7), wherein the part comprises a cell or cytoplasm of the plant.

(9) A cybrid plant of the genus *Lactuca*, a progeny thereof or a part thereof, comprising, in cytoplasm thereof, a gene derived from mitochondria of a plant of the genus *Helianthus*.

(10) The cybrid plant of the genus *Lactuca*, or the progeny thereof, or the part thereof according to (9), wherein the plant of the genus *Helianthus* is *H. annuus L.* or a cytoplasm substitution line of *H. annuus L.* with cytoplasm from *H. petiolaris, H. argophyllus, H. debilis, H. decapetalus, H. giganteus, H. rigidus, H. salicifolius, H. anomalus, H. bolanderi, H. exilis, H. maximiliani, H. neglectus, H. praecox* or *H. tuberosus*.

(11) The cybrid plant of the genus *Lactuca*, or the progeny thereof, or the part thereof according to (9) or (10), wherein the cybrid plant of the genus *Lactuca* is derived from *Lactuca sativa L., L. serriola, L. aculeate, L. scarioloides, L. azerbaijanica, L. georgica, L. dregeana, L. altaica, L. saligna, L. virosa, L. tatarica, L. indica* or *L. debilis* or the interspecific hybrid plant thereof.

(12) The cybrid plant of the genus *Lactuca*, or the progeny thereof, or the part thereof according to any one of (9) to (11), wherein the gene derived from mitochondria of a plant of the genus *Helianthus* is a male sterile gene.

(13) The cybrid plant of the genus *Lactuca*, or the progeny thereof, or the part thereof according to any one of (9) to (12) which is cytoplasmic male sterile.

(14) The part of the cybrid plant of the genus *Lactuca* or the progeny thereof according to any one of (9) to (13), wherein the part comprises a cell or cytoplasm of the plant.

(15) A seed of the cybrid plant of the genus *Lactuca* that has been deposited under Accession No. FERM BP-10421, a cybrid plant of the genus *Lactuca* grown from the seed, or the progeny thereof, or a part thereof.

(16) The part of the cybrid plant of the genus *Lactuca* or the progeny thereof according to (15), wherein the part comprises a cell or cytoplasm of the plant.

(17) A seed of the cybrid plant of the genus *Lactuca* that has been deposited under Accession No. FERM BP-10647, a cybrid plant of the genus *Lactuca* grown from the seed, or the progeny thereof, or a part thereof.

(18) The part of the cybrid plant of the genus *Lactuca* or the progeny thereof according to (17), wherein the part comprises a cell or cytoplasm of the plant.

(19) A method for producing first filial generation seed, comprising: crossing, as a seed parent, the cybrid plant of the genus *Lactuca* produced by the method according to (6), or the progeny thereof, with, as a pollen parent, a plant of the genus *Lactuca* that is crossable with the cybrid plant; and harvesting first filial generation seed produced by the seed parent after the crossing.

(20) A method for producing first filial generation seed, comprising: crossing, as a seed parent, the cybrid plant of the genus *Lactuca* according to (13), or the progeny thereof, with, as a pollen parent, a plant of the genus *Lactuca* that is crossable with the cybrid plant; and harvesting first filial generation seed produced by the seed parent after the crossing.

(21) A method for producing first filial generation seed, comprising: crossing, as a seed parent, the cybrid plant of the genus *Lactuca* according to (15), or the progeny thereof, with, as a pollen parent, a plant of the genus *Lactuca* that is crossable with the cybrid plant; and harvesting first filial generation seed produced by the seed parent after the crossing.

(22) A method for producing first filial generation seed, comprising: crossing, as a seed parent, the cybrid plant of the genus *Lactuca* according to (17), or the progeny thereof, with, as a pollen parent, a plant of the genus *Lactuca* that is crossable with the cybrid plant; and harvesting first filial generation seed produced by the seed parent after the crossing.

(23) A first filial generation seed produced by the method according to any one of (19) to (22), or a first filial generation plant grown from the seed.

This description includes the contents of the specification and/or the drawings of Japanese Patent Application No. 2005-311598, which is the base of the priority of this application.

BRIEF DESCRIPTION OF THE DRAWINGS

FIG. 1 is a photograph of electrophoresis showing the result of PCR using the primers specific for the sunflower mitochondrial genes orf522 (top) and orf873 (bottom), and DNA extracted from 2 lines of cytoplasmic male sterile sunflower, 1 line of male fertile sunflower, and 13 cultivated varieties of lettuce as test materials;

FIG. 8 is a photograph of electrophoresis showing the result of PCR with the primers specific for the sunflower mitochondrial gene orf873, to test extracted DNA from leaves of the 14 individuals at BC3 generation of the cytoplasmic male sterile lettuce;

FIG. 9A is a photograph of electrophoresis showing the result of PCR with the primers specific for the mitochondrial genes atp6, cox II, and cob to test DNA extracted from leaves of the 14 individuals at BC3 generation of the cytoplasmic male sterile lettuce. For the mitochondrial genes atp6, cox II, and cob the result shown is that of PCR-RFLP in which the PCR amplification products were further digested with a restriction enzyme(s);

FIG. 9B is a photograph of electrophoresis showing the result of PCR with the primers specific for the mitochondrial genes rps3, trnN, trnY, trnS, and trnP, to test DNA extracted from leaves of the 14 individuals at BC3 generation of the cytoplasmic male sterile lettuce;

BEST MODE FOR CARRYING OUT THE INVENTION

Figure 2:
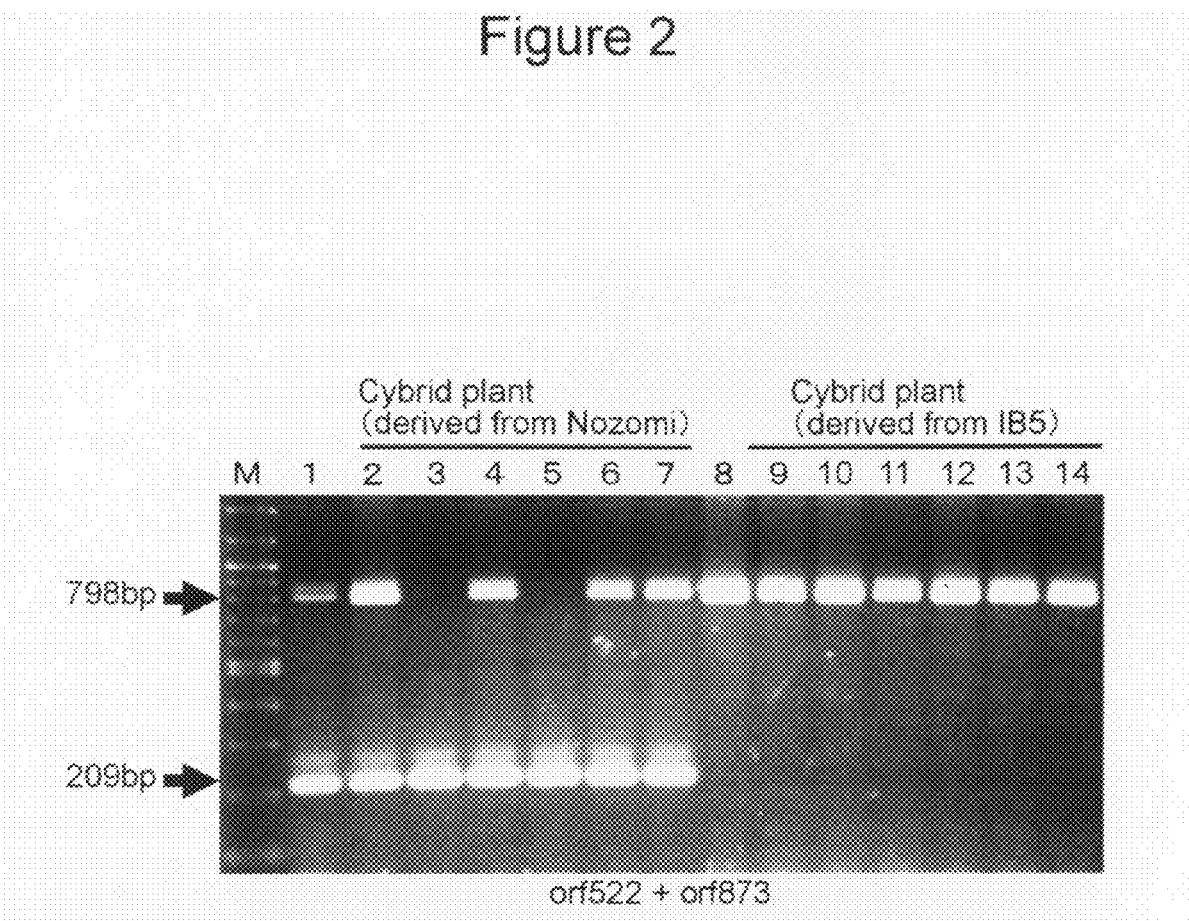
FIG. 2 is a photograph of electrophoresis showing an exemplary result of testing of the cybrid plants using the primers specific for the sunflower mitochondrial genes orf522 and orf873.

A fused hybrid cell and a cybrid plant according to the present invention can be produced by the method comprising the following steps:
(1) preparation of protoplasts;
(2) fusion treatment of protoplasts;
(3) culture of fused hybrid cells;
(4) regeneration of plants from microcalli;
(5) selection of cybrid plants;
(6) selection of favorable lines;
(7) use of cytoplasmic male sterile plants and the production of F1 seed.

The details of each step are as follows.
(1) Preparation of Protoplasts
(i) Isolation of Protoplasts from a Plant of the Genus *Lactuca*

Preferably, the plant of the genus *Lactuca* for the preparation of protoplasts is *Lactuca sativa L., L. serriola, L. aculeate, L. scarioloides, L. azerbaijanica, L. georgica, L. dregeana, L. altaica, L. saligna, L. virosa, L. tatarica, L. indica* or *L. debilis*, or an interspecific hybrid plant thereof, and particularly *L. sativa L.*, which is a cultivated species of lettuce. *L. sativa L.* is classified into var. angustana (including asparagus lettuce, stem lettuce, etc.), var. longifolia (including cos, romaine lettuce, etc.), var. crispa (including leaf lettuce, loose leaf lettuce, etc.), var. capinata (head lettuce, butter head lettuce, crisphead, cabbage lettuce, etc.) and the like, and these are all varieties in the same species differentiated by ecological differences. In the present invention, any variety of *L. sativa L.* may be suitably used. Although endive, chicory, etc. have similar characteristics to lettuce, they are not included in lettuce because they are not in the genus *Lactuca* ("Vegetable Horticulture Encyclopedia 7: Lettuce and Celery (in Japanese)" 1st ed., p. 87, Rural Culture Association, published on Apr. 30, 1989).

The cellular tissue used to obtain protoplasts is desirably mesophyll tissue, which provides high yield and is highly active in cell division, but other tissue such as hypocotyl, stalk, and callus may be used as a material.

The method for isolating protoplasts is not limited to a particular method, but may be one of those that is commonly used (Non-patent Documents 8 and 18). First, a cellular tissue of lettuce is cut into fine pieces, and treated with a enzyme(s) to isolate protoplasts. Here, an enzyme solution for the protoplast isolation is used. This solution is an inorganic salt buffer that contains mainly a cell-wall-digesting enzyme(s) and an osmoticum. This cell-wall-digesting enzyme is not limited to particular enzymes, but may be any enzyme that can be used to digest a plant cell wall, including cellulase, hemicellulase, pectinase, etc. In the present invention, the combination of Meicelase and Maserozyme R-10 is preferably used. An osmoticum may be a usual sugar alcohol, for example, mannitol, sorbitol, glucose etc., and is preferably mannitol, and more preferably mannitol at 0.3 to 0.7 M in concentration. Also, inorganic salts are desirably added to the enzyme solution to stabilize the membrane of protoplasts. For example, the addition of CPW salts solution (Cocking and Peberdy, 1974), which composition is shown in Table 1, is preferable. Preferably, the enzymatic treatment is performed at 25 to 30° C. for 8 to 20 hours without moving.

TABLE 1

| Composition of CPW salts solution | |
|---|---|
| $KH_2PO_4$ | 27.2 mg/l |
| $KNO_3$ | 101.0 mg/l |
| $CaCl_2 \cdot 2H_2O$ | 1,480.0 mg/l |
| $MgSO_4$ | 246.0 mg/l |
| KI | 0.16 mg/l |
| $CuSO_4 \cdot 5H_2O$ | 0.025 mg/l |
| Mannitol | 0.6 M |
| pH | 5.8 |

The protoplasts isolated by the enzymatic treatment are filtered through nylon mesh with the pore size of 30 to 100 μm, centrifuged, and harvested to remove the enzyme solution. Then, the protoplasts are suspended into a washing solution, and washed. While the washing solution may be a CPW salts solution with sugar alcohol added as an osmoticum as commonly used, in this example the solution S, which composition is shown in Table 2, is preferably used as the washing solution because the solution S is desirably used when the protoplasts are fused with protoplasts derived from a plant of the genus *Helianthus*, which are isolated later on (for reference, see Lenee P, Chupeau Y (1986) Plant Sci. 43: 69-75).

TABLE 2

| Composition of the solution S | |
|---|---|
| CaCl$_2$•2H$_2$O | 2,000 mg/l |
| KCl | 250,000 mg/l |
| MES | 700 mg/l |
| pH | 5.6 |

Then, an inactivation treatment is desirably performed to prevent the cell division of protoplasts of the plant of the genus *Lactuca*. The inactivation treatment may be carried out by suspending the protoplasts to a CPW salts solution, etc. that contains iodine compounds such as iodoacetic acid and iodoacetamide. In the present invention, the inactivation treatment is preferably carried out by suspending the protoplasts to a CPW solution that contains iodoacetamide at 5 to 30 mM in concentration, and incubating for 5 to 20 minutes.

Then, the protoplasts are preferably washed with the solution S 1 to 3 times by centrifugation. The protoplasts are further purified by density gradient centrifugation, etc., because fragments of vessels and cells contaminate the protoplast suspension. Sugar, synthetic colloid, etc., may be used as a reagent in the purification. In the present invention, a sucrose solution is preferably used, and more preferably a sucrose solution at 15 to 20% is used. After the purification of protoplasts, the cell density is measured with a hemocytometer, and the volume of the suspension is adjusted with the solution S to have a suitable cell density for the protoplast fusion. The preferred cell densities of the protoplast suspension are 1×10$^5$ to 1×10$^7$ cells/ml, and the solution S is preferably used to adjust the volume.

(ii) Isolation of Protoplasts from a Plant of the Genus *Helianthus*

A plant of the genus *Helianthus* may be used as the donor material to provide cytoplasm in the present invention. In the genus *Helianthus*, particularly preferred is *Helianthus annuus* L., which is a cultivated variety of sunflower, or a cytoplasm substitution line of *H. annuus* L. with cytoplasm from *H. petiolaris*, *H. argophyllus*, *H. debilis*, *H. decapetalus*, *H. giganteus*, *H. rigidus*, *H. salicifolius*, *H. anomalus*, *H. bolanderi*, *H. exilis*, *H. maximiliani*, *H. neglectus*, *H. praecox* or *H. tuberosus*.

The plant of the genus *Helianthus* used in the present invention is preferably a cytoplasmic male sterile line. Conventionally, many cytoplasmic male sterile lines have been produced in *H. annuus* L. It is known that they are derived from natural mutations or the progeny of various interspecific hybridizations in cultivated species. In particular, cytoplasmic male sterile lines derived from natural mutants of *H. annuus* L., or various cytoplasm substitution lines of *H. annuus* L. are known, and their divergence has been shown using techniques in molecular biology (Non-patent Document 10). Thus, many cytoplasm substitution lines that exhibit cytoplasmic male sterility have been already obtained. In the present invention, various cytoplasm substitution lines of the genus *Helianthus* may be used as the donor material to provide cytoplasm.

To obtain a cybrid plant of the genus *Lactuca* with cytoplasmic male sterility according to the present invention, plants of the genus *Helianthus* that have a cytoplasmic male sterile gene are preferably, but not exclusively, used as the donor material to provide cytoplasm. When protoplasts from a plant of the genus *Helianthus* and protoplasts from a plant of the genus *Lactuca* are fused, the lines that express cytoplasmic male sterility can be obtained as a result of the recombination or rearrangement between mitochondrial genomes of those plants. The resultant hybrid plants of the genus *Lactuca* that are cytoplasmic male sterile are also encompassed by the present invention.

The inactivation of nuclear genome may be also performed by irradiation to the cells of the plants of the genus *Helianthus* that are used in the protoplast fusion. As a result of the inactivation of the nuclear genome in the cells of the genus *Helianthus*, the regeneration after the fusion of cells of the genus *Helianthus* and the genus *Lactuca* occurs without any influence of the nuclear genome in the plant of the genus *Helianthus*, but with the redifferentiation ability of the nuclear genome of the genus *Lactuca*, the regeneration of a plant of the genus *Lactuca* that has the cytoplasmic genes of the plant of the genus *Helianthus* become possible.

In the present invention, various material plants of the genus *Helianthus* can be chosen as the donor cells to provide cytoplasm, as described above, and it is possible to produce cybrid plants of the genus *Lactuca* with various genetic backgrounds.

To prepare protoplasts from a plant of the genus *Helianthus*, a cellular tissue of the plant of the genus *Helianthus* is first cut into fine pieces, and soaked in an enzyme solution for the protoplast isolation to isolate the protoplasts. The cellular tissue to be used is preferably hypocotyl, because of the high yield and the robustness of cell membrane, but other tissues such as leaf and stalk may be used as material. Cell-wall-digesting enzymes are not limited to particular enzymes, but may be any enzyme that can be used to digest a plant cell wall; the combination of Driserase and Maserozyme R-10 is preferably used in the present invention. Also, the cell-wall-digesting enzymes are preferably used in a solution which osmotic pressure is adjusted with inorganic salts such as KCl and NaCl, because the protoplasts isolated from hypocotyl in the plant of the genus *Helianthus* have low specific gravities. For example, the solution S is preferably used in the present invention. Preferably, the enzymatic treatment is performed at 25 to 30° C. for 8 to 20 hours without moving. The protoplasts isolated by the enzymatic treatment are filtered through nylon mesh with the pore size of 30 to 100 µm. Because the nuclear genes in the protoplasts derived from the plant of the genus *Helianthus* are not required, the nuclear genes in the isolated protoplasts are desirably inactivated by irradiation. Irradiation is not limited to a particular kind, but may be of any kind that can inactivate nuclear genes, including X ray, gamma ray, and ultraviolet, etc. Preferably, the amount of irradiation is the lowest in the range that is enough to inactivate the nuclei. For example, the preferred amounts of irradiation are 0.1 to 0.6 Gy of soft. X-ray in the present invention.

(2) Fusion Treatment of Protoplasts

Then, the protoplasts of the two kinds that received the inactivation treatment as described above are fused. The method of fusion is not limited to particular methods, but may be one of publicly known methods including electrofusion (Planta, 151, 26-32, 1981), PEG method (Planta, 120, 215-227, 1974), and dextran method (Jap. J. Genet., 50, 235, 1975), etc. In the present invention, a modified PEG method is preferably used.

(3) Culture of Fused Hybrid Cells

The cells received the fusion treatment are preferably cultured in a medium suitable to culture protoplasts from a plant of the genus *Lactuca*. Many methods are known for culturing protoplasts from a plant of the genus *Lactuca,* and any method may be adequately used in the present invention. In particular, a modified method of a publicly known method (Nishio, T., et al., Japanese journal of breeding, 38,165-171) is preferably used in the present invention. The method by Nishio et al. is an excellent method that is efficient for culturing protoplasts from plants of the genus *Lactuca.* However, this method by Nishio et al. is not applicable to the present invention without any modification. Nishio et al. reported culturing of protoplasts from a single plant of the genus *Lactuca,* and those protoplasts did not receive any fusion treatment and therefore they had little damage to their cell membrane. This made it possible to culture those protoplasts on a solid medium containing gellan gum from the beginning of culturing. In the present invention, the cell membrane of cells to be cultured after the fusion treatment is fragile due to the stress of the treatment. Therefore it is difficult to culture fused cells efficiently in the method by Nishio et al., because those cells burst when mixed with gellan gum. Accordingly, the cells after the fusion treatment are suitably cultured first in a liquid medium that does not contain gellan gum to facilitate the restoration of cell membrane before adding gellan gum to the medium after 3 to 7 days of culturing. This modification to the method by Nishio et al., allows efficient culturing of fused cells. Fused cells are suitably passaged in a fresh medium with lowered osmotic pressure because they form microcalli through repeated cell divisions.

(4) Regeneration of Plants from Microcalli

When microcalli have grown to several millimeters in size, they are transferred to a redifferentiation medium and allowed to regenerate. The responses to redifferentiation medium may be differed depending on the material plant of the genus *Lactuca* and the status of microcalli. For example, it is suitable to use MS medium (Murasige, T. & Skoog, Physiol. Plant., 15, 473-497 (1962)) containing 0.3 to 1.0 mg/l of BA or a similar medium. The regenerated shoots are transferred to a rooting medium, for example MS medium of ½ concentrations, allowed to regenerate into a plant. The regenerated plants are planted in a greenhouse after the acclimatization.

(5) Selection of Cybrid Plant

DNA is extracted from leaves of the plants regenerated according to the procedure described above, and the plants of the genus *Helianthus* and the genus *Lactuca* are used as the material plants. For example, cybrid plants into which the mitochondrial genes from *H. annuus L.* are introduced can be distinguished by using PCR to detect the mitochondrial genes specific for *H. annuus L.,* such as orf522, orf708, or orf873 as a marker. First, primers that specifically amplify the target gene are designed to perform PCR. Then, electrophoresis is performed to confirm the expected size of band.

In this way, the individuals with a plant of the genus *Lactuca* and the mitochondrial DNA of a plant of the genus *Helianthus* introduced into the plant can be selected. Furthermore, PCR-RFLP (Tsumura, Y., Yoshimura, K. Tomaru, N. et al., Theor. Appl. Genet. 91, 1222-1236, 1995) may be used to detect the mitochondrial DNA from the plant of the genus *Helianthus* by distinguishing it from the mitochondrial DNA from the plant of the genus *Lactuca.*

Desirably, PCR-RFLP is also used to confirm that the chloroplasts of the cybrid plants selected by the PCR analysis are derived from the plant of the genus *Lactuca.* Chloroplast genes that can be used for PCR-RFLP are not limited to particular genes, but may be any gene that can be used to detect the polymorphism between plants of the genus *Helianthus* and the genus *Lactuca,* including rbcL, matK, etc. Primers that specifically amplify the target chloroplast gene region are designed to perform PCR. The amplified product of PCR is treated with a restriction enzyme(s), and RFLP due to the differences of the restriction enzyme sites is detected to confirm the origin of the chloroplasts. The individuals with the chloroplasts from the plant of the genus *Lactuca* are desirably selected in the view of compatibility with the nuclear genes.

The DNA confirmation as described above may be performed when they are calli as well as after the acclimatization of the plants. Furthermore, it is desirable to assess the ploidy by flow cytometry or by observing the chromosomes.

(6) Selection of Favorable Lines

The resultant cybrid plants are screened for male sterile lines without morphological abnormalities in other organs. It is especially important to select the lines with higher female fertility, as female fertility, i.e. the seed production, tends to decrease, when there is a defect in the genital organ, such as male sterility. An efficient selection can be achieved by analyzing the mitochondrial genome of cybrid plants by PCR-RFLP analysis, etc. and using the data for the selection. For example, when some of the mitochondrial genes of the plant of the genus *Helianthus* are introduced into an individual, so that male sterility is expressed in the individual, though many mitochondrial genes in the individual are still the same as the plant of the genus *Lactuca,* the individual has higher compatibility with the nucleus of the plant of the genus *Lactuca,* and therefore a higher probability exists that the traits other than male sterility are normal.

Furthermore, the selected male sterile individuals are crossed with pollen of the lettuce with normal cytoplasm to confirm that male sterility is transmitted to the hybrid progeny by cytoplasmic inheritance. Also, many hybrid progenies are grown under various environments to confirm that male sterility is stable.

In order to enhance the possibility of selecting favorable lines, a technique of increasing the number of the cybrid plants of the genus *Lactuca,* which are candidates for the selection, is effective. In addition, a technique of primarily selecting favorable plant lines having cytoplasmic male sterility from a relatively small number of the cybrid plants of the genus Lactuca as candidates and then further improving the cytoplasm of the selected favorable plant lines is also effective for obtaining desirable favorable lines. Either of the above two techniques can select favorable lines. Furthermore, a combination of both techniques can be employed. A preferable method of further improving the cytoplasm of a cytoplasmic male sterile cybrid plant of the genus *Lactuca* is, for example, use of a cytoplasmic male sterile cybrid plant of the genus *Lactuca* as donor material to provide cytoplasm and performing asymmetric protoplast fusion with a lettuce of interest. Such asymmetric protoplast fusion causes, for example, recombination or rearrangement of the mitochondrial genome to enhance the possibility of selecting lines that maintain the cytoplasmic male sterility and include cytoplasm having higher compatibility with the nuclear gene of the lettuce.

A cybrid plant of the genus *Lactuca* that is produced and selected by the procedure described above comprises, in cytoplasm thereof, a gene(s) derived from cytoplasm, preferably mitochondria of a plant of the genus *Helianthus.* The pertinent cybrid plant of the genus *Lactuca* comprises the nuclear genome of the plant of the genus *Lactuca,* and preferably further comprises the chloroplast genome of the plant of the genus *Lactuca.* The present invention also relates to the pertinent cybrid plant of the genus *Lactuca,* the progeny thereof, or a part thereof. In the present invention, "the progeny of the cybrid plant of the genus *Lactuca*" means the cybrid plants of the genus *Lactuca* in the next generation and generation after next that succeed the pertinent cytoplasm by cytoplasmic inheritance, and that are obtained by crossing the pollen from a plant of the genus *Lactuca* that is crossable with the cybrid plant of the genus *Lactuca*. In the present invention, "a part of the cybrid plant of the genus *Lactuca* or the progeny thereof" comprises one or more cells of the pertinent plant, or cytoplasm from the one or more cells, and in particular it means an organ(s) or tissue(s) such as a flower, leaf, stalk and root; or a cell(s) (including a protoplast(s) prepared from the cell(s)) or cytoplasm from these organ(s) or tissue(s); or an aggregate of the aforementioned cells or cytoplasm.

(7) Use of Cytoplasmic Male Sterile Plants and the Production of F1 Seed

Favorable lines with cytoplasmic male sterility can be obtained by successive backcross of favorable plants of the genus *Lactuca* to the cytoplasmic male sterile cybrid plants of the genus *Lactuca* produced by the method according to the present invention. The resultant favorable lines with cytoplasmic male sterility may be used as a seed parent to produce F1 seed.

More preferably, seed parents with cytoplasmic male sterility can be created in a short time by using the cytoplasmic male sterile cybrid plants of the genus *Lactuca* produced by the present invention as donor material to provide cytoplasm, and by performing asymmetric protoplast fusion between the donor material and a lettuce of interest. Such asymmetric protoplast fusion causes, for example, recombination or rearrangement of the mitochondrial genome, and lines maintaining the cytoplasmic male sterility and including cytoplasm having higher compatibility with the nuclear gene of the lettuce can be selected.

In addition, cytoplasm of the cytoplasmic male sterile cybrid plants of the genus *Lactuca* produced by the present invention can be also introduced into other species of the genus *Lactuca*. Approximately 100 wild species are known in plants of the genus *Lactuca*, and the cultivated lettuce variety *L. sativa* is crossable with 9 wild species in the subsection *Lactuca*: *L. serriola, L. aculeate, L. scarioloides, L. azerbaijanica, L. georgica, L. dregeana, L. altaica, L. saligna*, and *L. virosa* (Patent Document 17).

If crossable, the substitutions of cytoplasm and the nucleus can be easily achieved by a conventional breeding technique of successive backcrossing to create novel combinations of cytoplasm and nucleus (nuclear substitution). Thus, cytoplasm that expresses cytoplasmic male sterility can be easily introduced into these wild species or interspecific hybrids by crossing them with a cytoplasmic male sterile cybrid plant of the genus *Lactuca* produced by the present invention. Moreover, the scope of applicability can be expanded by embryo and ovule culture. Furthermore, in the genus *Lactuca,* many somatic hybrids with wild species have been created by protoplast fusion for the purpose of introducing useful traits of the wild species (for example, Patent Document 17; Plant cell reports 9: 531-534 (1991); and Non-Patent Document 18). Such wild species include, for example, *L. tatarica, L. virosa, L. indica, L. debilis,* etc., and cytoplasm of the cytoplasmic male sterile cybrid plants of the genus *Lactuca* produced by the present invention can be introduced into many of the wild species of the genus *Lactuca* and their interspecific hybrids using these protoplast fusion techniques. The introduction of cytoplasm can be done more efficiently by irradiating and inactivating the nuclei of cytoplasmic male sterile cybrid plants of the genus *Lactuca* produced by the present invention, and using them as cytoplasm donor cells to perform asymmetric protoplast fusion. Thus, cytoplasm of the cytoplasmic male sterile cybrid plants of the genus *Lactuca* produced by the present invention can be introduced into many plants of the genus *Lactuca* using conventional techniques such as successive backcrossing and protoplast fusion techniques. Conveniently, cytoplasmic male sterility can be also introduced into an interspecific hybrid plant of the genus *Lactuca* into which useful genes of wild species have been introduced.

Accordingly, the efficient F1 seed production of plants of the genus *Lactuca* can be achieved by using, as a seed parent, a cytoplasmic male sterile cybrid plant of the genus *Lactuca* produced by the present invention, or the progeny that are created or produced from the pertinent plant by the procedures described above; crossing them with a crossable plant of the genus *Lactuca* as a pollen parent; and harvesting first filial generation seed produced by the seed parent after the crossing. The method of crossing is not limited to any particular method, but may be any conventional method that allows the pollination of pollen from the pollen parent line to the pistils of the seed parent, including, for example, wind pollination, insect pollination (for example, Patent Document 20), and artificial crossing in which pollen from the pollen parent line are placed manually on the pistils of the seed parent. A preferably selected method is an economical method suited to the region and facility of the seed production.

The production of F1 varieties of lettuce according to the above procedures enables the rapid breeding of lettuce varieties with favorable traits, and the production of marketable lettuce varieties with uniform product quality and superior adaptability to the environment, etc.

The present invention is described in detail with the following examples, but is not limited to these examples.

EXAMPLE 1

(1) Preparation of Protoplasts
(i) Isolation of Lettuce Protoplasts

This example describes a procedure using the lettuce variety 'Tell me' (Sakata Seed). Sterilized seeds were plated on MS medium supplemented with 10 g/L sucrose and 8 g/L agar, and cultured for one month at 20° C. with 16 hours of light a day. Approximately 1 g of opened leaves were harvested, and cut into pieces of about 2 mm in size. They were soaked in 10 ml of CPW salts solution containing 0.4% Meicelase, 0.08% Maserozyme R-10, and mannitol, and incubated at 25° C. for 16 hours without moving.

The protoplast suspension was filtered through 92 micrometer nylon mesh, and centrifuged at 500 rpm for 3 minutes. After removing the supernatant, the pellet was resuspended into 2 ml of Solution S containing 15 mM iodoacetamide, and incubated at 25° C. for 5 minutes without moving. The iodoacetamide-treated protoplasts were centrifuged at 300 rpm for 3 minutes, and resuspended into 10 ml of Solution S after removing the supernatant, and washed 3 times with Solution S. After centrifugation at 300 rpm for 3 minutes, the supernatant was removed and the pellet was resuspended into CPW salt solution containing 20% sucrose in a final volume of 9.5 ml. 0.5 ml of Solution S was layered on the suspension and this was centrifuged at 1000 rpm for 5 minutes.

The purified protoplasts, which moved into the upper layer in Solution S, were collected into a centrifuge tube with a Pasteur pipette. The protoplasts were suspended into 2 ml of Solution S and a small amount of the suspension was removed for determining the cell density of the protoplast suspension using a hemacytometer. Solution S was added to the suspension to $1 \times 10^6$ cells/ml.

(ii) Isolation of Sunflower Protoplasts

This example describes a procedure using the cultivated variety "Nozomi" (Sakata Seed) (which have the sunflower specific genes orf522 and orf873) sunflower for cut flower and the breeding line "IB5" (which has one of the sunflower specific genes, gene orf873, but not orf522) of sunflower for cut flower. Sterilized seeds were plated on MS medium supplemented with 10 g/L sucrose and 8 g/L agar, and cultured at 25° C. in dark for 7 days. When the hypocotyls had grown to about 50 mm, they were cut into 1 cm in length, and further divided into halves along the direction of the hypocotyl elongation. Cut pieces from about 10 hypocotyls were soaked in 10 ml of Solution S containing 0.5% Cellulase Onozuka R-10 and 0.1% Maserozyme R-10, and incubated for 16 hours without moving.

The protoplast suspension was filtered through 92 micrometer nylon mesh. In a centrifuge tube, 2 ml of CPW salts solution containing 17% sucrose was transferred, and the protoplast suspension was layered on it. After centrifuge at 1200 rpm for 5 minutes, the purified protoplasts were gathered in a band, and the upper layer above the band was removed carefully avoiding the aspiration of protoplasts. The protoplasts were suspended in a final volume of 9.5 ml by adding CPW salt solution containing 17% sucrose. 0.5 ml of Solution S was layered on the suspension and this was centrifuged at 1200 rpm for 5 minutes.

Protoplasts, which moved into the upper layer in. Solution S, were collected with Pasteur pipette, transferred into a plastic dish and exposed to soft X-ray at 0.5 Gy. The protoplast suspension exposed to the soft X-ray was transferred into a centrifuge tube, and brought up to 9.5 ml with CPW salts solution containing 17% sucrose. 0.5 ml of Solution S was layered on the suspension and this was centrifuged at 1200 rpm for 5minutes. The protoplasts that moved into the Solution S layer were transferred into a centrifuge tube, and the suspension was brought up to 10 ml with Solution S. A small amount of the suspension was removed for determining the cell density of the protoplast suspension using hemacytometer. Solution S was added to the suspension to $3 \times 10^6$ cells/ml.

(2) Fusion Treatment of Protoplasts

The equal volumes of the lettuce protoplast suspension treated with iodoacetamide and the sunflower protoplast suspension irradiated with soft X-ray were mixed and 2 ml of the mixture was dropped onto the center of the bottom of 9 cm dish. After incubation for 30 minutes without moving, 3 ml of PEG solution (300 g/l PEG3350, 1,500 mg/l $CaCl_2$-$2H_2O$, and 100 mg/l $KH_2PO_4$, pH 5.5) was added dropwise around the protoplast mixture.

1 minute later 3.5 ml of CPW salts solution was added dropwise around the protoplast mixture. Further 2 minutes later, 3.5 ml of CPW salts solution was added dropwise around the protoplast mixture again. 5 minutes later, the liquid added dropwise was removed at the edge of the dish by careful aspiration. 20 ml of CPW salts solution was added at the edge of the dish. This washing with CPW salts solution was repeated three times at five minutes intervals.

(3) Culture of Fused Hybrid Cells

After removing the washing solution, 10 ml of ½ concentration MS medium (pH 5.8) containing 2.7 g/l disodium succinate hexahydrate, 1.0 g/l casamino acid, 1.0 mg/l NAA, 0.3 mg/l BA, and 0.3 M sucrose with reduced $NH_4NO_3$ concentration to 200 mg/l (hereinafter, referred to as culturing medium for lettuce protoplast) was added to the protoplasts, they were cultured at 25° C. in dark.

3 days after the start of culturing, 5 ml of 4 times-concentrated culturing medium for lettuce protoplast (with 0.3 M sucrose) and 5 ml of 0.3 M sucrose solution (pH 5.8) containing 0.6% gellan gum were mixed, and culture was continued in this medium mixture in semisolid gel.

10 days after the start of culturing, 10 ml of culture containing fused hybrid cells were transferred along with the gel into 10 ml of culturing medium for lettuce protoplast in which sucrose concentration was modified to 0.15 M. 20 days after the start of culturing, when microcalli had become visible to the naked eye, they were transplanted onto the culturing medium for lettuce protoplast containing 1.0% sucrose and 0.3% gellan gum (solid medium, pH 5.8).

(4) Regeneration of Plants from Microcalli 30 days after the start of culturing, when microcalli were about 2 mm in size, they were transferred onto MS medium (pH 5.8) containing 0.1 mg/l NAA, 0.3 mg/l BA, 1.0% sucrose, and 0.8% agar. 40 to 60 days after the start of culturing, the shoots redifferentiated from the calli were transferred onto ½ MS medium (pH 5.8) containing 1.0% sucrose and 0.8% agar, and they grew roots and regenerated into the cybrid plants. The cybrid plants were transferred to vermiculite, acclimatized and grown in a greenhouse.

(5) Selection of Cybrid Plants that have a Sunflower Specific Mitochondrial Gene Total DNA was extracted from leaves of the cybrid plants according to a method known in the art (Jhingan, A. K. (1992) Methods in molecular and cellular biology 3: 15-22). To detect sunflower specific DNA by PCR, primers specific for the orf522 and orf873 genes (Table 3) were designed based on the nucleic acid sequence information publicly available in the art (Gene Bank Accession Nos. Z23137 and X62592). The combinations of primers orf522-F and orf522-R, primers orf873-F and orf873-R were used for PCR using extracted whole genome DNA as a template. PCR was performed with 35 cycles of denaturation at 94° C for 1 minute, annealing at 60° C for 2 minutes, and elongation at 72° C for 2 minutes. PCR products were separated by electrophoresis in 1.8% agarose gel, soaked in ethidium bromide solution, and photographed under UV light to determine whether bands with expected sizes of 209 by and 798by were present.

TABLE 3

Primers and their nucleic acid sequences used in the present invention

| Gene | Primer name | Sequence (5' to 3') |
|---|---|---|
| orf522 | orf522-F | cgtccttgcgtgagggtttg |
| | orf522-R | tgagtaccgttctctcacgagttg |
| orf873 | orf873-F | gctactcggacgaaaactaggaac |
| | orf873-R | cccaacttcacgcggaacag |
| rbcL | rbcL-F | tcaacctggagttccgcctgaag |
| | rbcL-R | gtgccctaaagttcctccaccgaa |
| atp6 | atp6-F | gctaactctcagtttggtcctac |
| | atp6-R | ccagaccggttaatgcaaga |
| coxII | coxII-F | ctggcttaccggtaatctccaa |
| | coxII-R | cttgcaagtttcccgcaaa |
| cob | cob-F | tcttctccacactgaatcagca |
| | cob-R | agaatgggcgttatggcaaag |
| rps3 | rps3-F | ggaaatccgatttcggtaag |
| | rps3-R | agggtccttttaagtggatg |
| trnN | trnN-F | gagcggtcggctgttaactg |
| trnY | trnY-R | cagatttacagtctgtcgcttttaacc |

TABLE 3-continued

Primers and their nucleic acid sequences used in the present invention

| Gene | Primer name | Sequence (5' to 3') |
|---|---|---|
| trnS | trnS-F | ggcattggtttgctaaatcgacatac |
| trnP | trnP-R | acctatggccctctgtaccc |

To examine the specific amplification of the target DNA fragments, DNA was extracted from 2 lines of cytoplasmic male sterile sunflower, 1 line of male fertile sunflower (the breeding line "OS06"), and 13 cultivated varieties of lettuce listed in Table 4, and PCR was performed using the primers specific for the sunflower mitochondrial genes orf522 and orf873. The results are shown in FIG. 1. FIG. 1 is a photograph of electrophoresis showing the result of PCR using the primers specific for the sunflower mitochondrial genes orf522 (top) and orf873 (bottom), and DNA extracted from 2 lines of cytoplasmic male sterile sunflower (lanes 1 and 2), 1 line of male fertile sunflower (lane 3), and 13 cultivated varieties of lettuce (lanes 4 to 16) as test materials (symbols in FIG. 1: M: molecular weight marker, 1: Nozomi, 2: IB5, 3: OSO6, 4: Tell me, 5: Steady, 6: Logic, 7: Miya, 8: V lettuce, 9: Santanasu, 10: Sirius, 11: Asure, 12: Brutus 7, 13: Spark, 14: Santos 2 2, 15: Dejero, 16: Souther). As shown in FIG. 1, the bands of orf522 (209 bp) and orf873 (798 bp) were detected in the sunflower cultivated variety "Nozomi", and the band of orf873 (798 bp) was detected in the sunflower breeding line "IB5". On the other hand, neither band was detected in all of the 13 lettuce varieties that were examined. This result confirmed that specific DNA amplification does not occur in PCR with the primers specific for orf522 and for orf873 using lettuce DNA as a template. Based on this result, it is possible to select the cybrid plants that have a mitochondrial gene specific for sunflower by extracting DNA from the plants obtained by asymmetric protoplast fusion, and performing PCR.

FIG. 2 shows an exemplary result of testing of the cybrid plants obtained by this example. FIG. 2 is a photograph of electrophoresis showing an exemplary result of testing of the cybrid plants using the primers specific for the sunflower mitochondrial genes orf522 and orf873 (symbols in FIG. 2: M: molecular weight marker, 1: Nozomi, 2 to 7: the cybrid plants produced by using "Nozomi" as a donor material to provide cytoplasm, 8: IB5, 9 to 14: the cybrid plants produced by using "IB5" as a donor material to provide cytoplasm). Two sunflower varieties "Nozomi" and "IB5" were used as a cytoplasm donor, and the production of cybrid plants was possible using either cytoplasm.

The band of orf873 was detected to be absent in lanes 3 and 5 in FIG. 2 despite that orf522 was introduced into such individuals. These may be a result of the recombination in mitochondria.

TABLE 4

Fertile lettuce varieties used for testing the specificity of primers

| No. | Variety name | Male sterility | Supplier |
|---|---|---|---|
| 1 | Tell me | Fertile | Sakata Seed Corporation |
| 2 | Steady | Fertile | Tsuruta Seed Co., Ltd. |
| 3 | Logic | Fertile | The Yokohama Nursery Co., Ltd. |
| 4 | Miya | Fertile | Sumika Agrotech Co., Ltd. |
| 5 | V lettuce | Fertile | Kaneko Seeds Co., Ltd. |
| 6 | Santanasu | Fertile | Sakata Seed Corporation |
| 7 | Sirius | Fertile | Sakata Seed Corporation |
| 8 | Asure | Fertile | Sumika Agrotech Co., Ltd. |
| 9 | Brutus 7 | Fertile | The Yokohama Nursery Co., Ltd. |
| 10 | Spark | Fertile | Watanabe Nouji Co., Ltd. |
| 11 | Santos 2 | Fertile | Fujii Seed Co., Ltd. |
| 12 | Dejero | Fertile | Sumika Agrotech Co., Ltd. |
| 13 | Souther | Fertile | TAKII & CO., LTD. |

Figure 3:
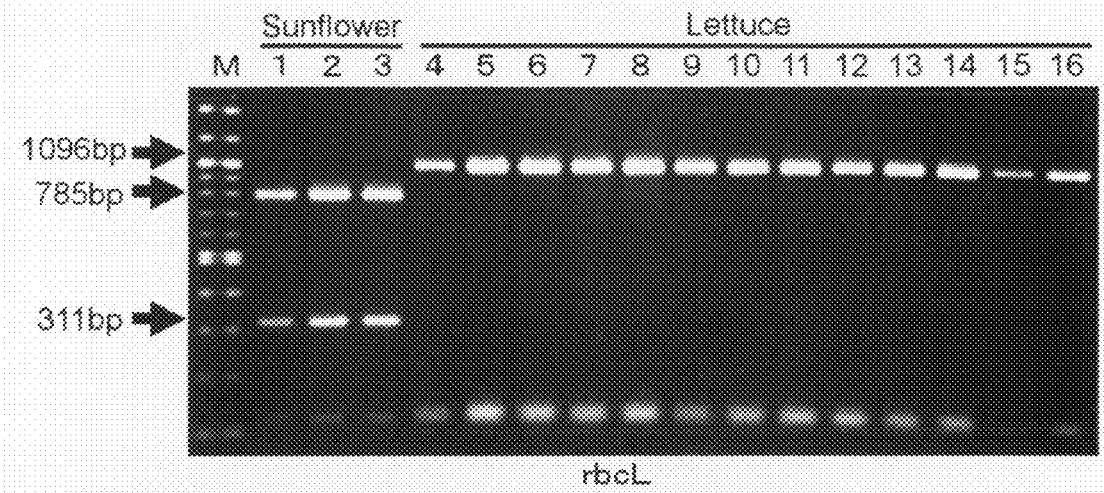
FIG. 3 is a photograph of electrophoresis showing PCR-RFLP pattern, in which DNA was extracted from 2 lines of cytoplasmic male sterile sunflower, 1 line of male fertile sunflower, and 13 cultivated varieties of lettuce as test materials, PCR was performed using the DNA templates and the primers specific for the chloroplast gene rbcL, and the amplified products were cut with TaqI.

In order to determine the source of chloroplasts by PCR-RFLP, primers specific for the sunflower chloroplast gene rbcL (Table 3) were designed based on the nucleic acid sequence information publicly available in the art (Gene Bank Accession No. L13929). PCR was performed with the primer combination rbcL-F and rbcL-R using extracted whole genome DNA as template. PCR was performed with 35 cycles of denaturation at 94° C. for 1 minute, annealing at 60° C. for 2 minutes, and elongation at 72° C. for 2 minutes. The PCR products were digested with the restriction enzyme TaqI, separated by electrophoresis in 1.8% agarose gel, soaked in ethidium bromide solution, and photographed under UV light, to determine how they were digested. Because the rbcL genes from sunflower and lettuce are highly homologous, and produce the amplified products of the same size, it was necessary to digest the PCR products with the restriction enzyme TaqI. The determination of the source of chloroplasts was made possible by detecting RFLP in the differences of the restriction enzyme sites. FIG. 3 is an photograph of electrophoresis showing PCR-RFLP pattern, in which DNA was extracted from 2 lines of cytoplasmic male sterile sunflower (lanes 1 and 2), 1 line of male fertile sunflower (lane 3), and 13 cultivated varieties of lettuce (lanes 4 to 16), PCR was performed using the DNA templates and the primers specific for the chloroplast gene rbcL, and the amplified products were cut with TaqI (symbols in FIG. 3: M: molecular weight marker, 1: Nozomi, 2: IB5, 3: OSO6, 4: Tell me, 5: Steady, 6: Logic, 7: Miya, 8: V lettuce, 9: Santanasu, 10: Sirius, 11: Asure, 12: Brutus 7, 13: Spark, 14: Santos 2 2, 15: Dejero, 16: Souther). As shown in FIG. 3, while the amplified product from the lettuce gene contains no restriction TaqI sites, and is thereby detected as a single band of 1096 by in size, the product from sunflower contains a restriction TaqI site, and is thereby detected as two bands of 311 by and 785 by in size. Therefore it was easy to distinguish the source of the chloroplasts. This result demonstrated that it was possible to select the cybrid plants with lettuce chloroplasts by extracting DNA from the plants obtained by asymmetric protoplast fusion and conducting PCR-RFLP.

(6) Selection of Cytoplasmic Male Sterile plants

Figure 4:
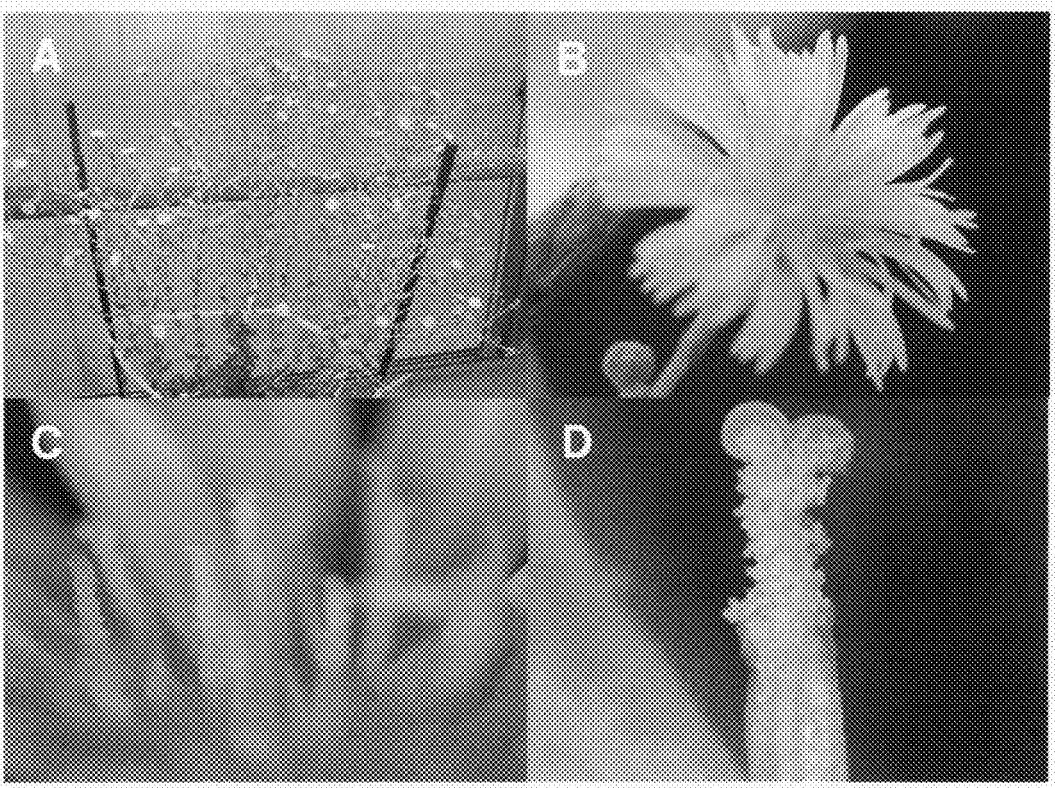
FIG. 4 shows the flower morphology of the cultivated lettuce variety "Tell me" (A: inflorescence, B: flower head, C: core of flower head (magnification×20) and D: pistil and anther tube (magnification×64))
Figure 5:
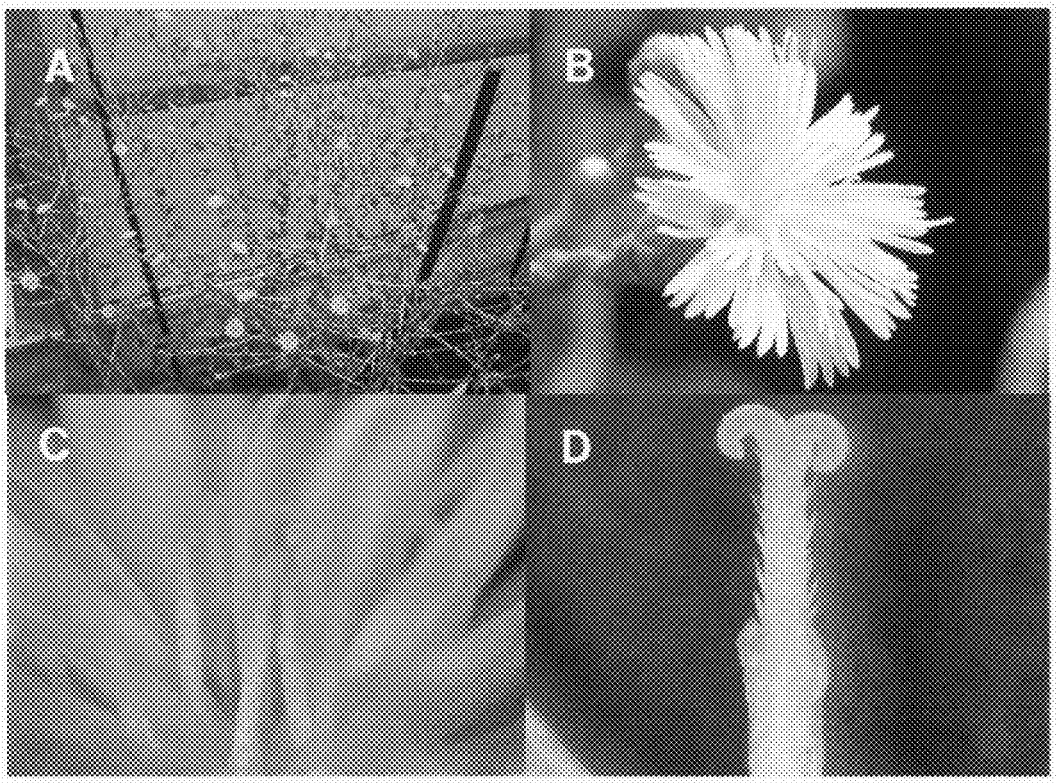
FIG. 5 shows the flower morphology of a cytoplasmic male sterile lettuce (A: inflorescence, B: flower head, C: core of flower head (magnification×20) and D: pistil with pollen adhered to it and anther tube (magnification×64))
Figure 6:
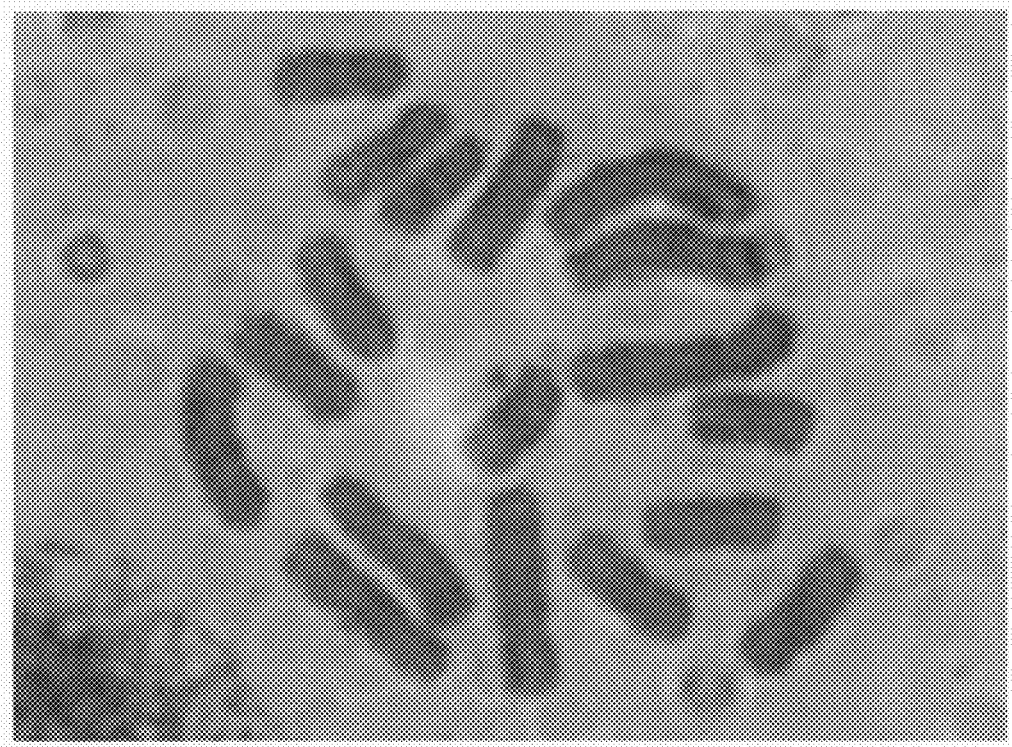
FIG. 6 shows an observation of the chromosomes of cytoplasmic male sterile lettuce.

Due to the incompatibility between the nuclear genes from lettuce and the mitochondrial genes from the introduced sunflower, many individuals of such cybrid plants show morphological abnormalities. Those individuals with a morphological abnormality were removed. Since the mitochondrial genome undergoes the recombination and rearrangement at high frequencies in protoplast fusion, morphological variations were observed in each individual of the regenerated plants. Because the flower organ is particularly susceptible to the morphological abnormalities due to the incompatibility, many cybrid plants were produced and screened for favorable lines that exhibit male sterility and normal morphologies in other aspects. Generally, lettuce exhibit protandry and it pollinates when the pistil is still elongating in the anther tube, therefore at the time of flowering a large amount of pollen is adhered to the pistil as shown in FIG. 4. For this reason, lettuce has very high rates of self-pollination. In the most desirable candidate of cytoplasmic male sterile line (hereinafter, referred to as "1216-2" (derived from the "IB5" of sunflower)) that was selected in the present invention, there was no pollen at all adhered on the pistil, and even in the anther tubes there was no sign of pollen, as shown in FIG. 5. Moreover, there was no clear difference observed in the morphologies of the flower organ and other organs. Furthermore, the investigation of the chromosome number confirmed that it was 2n=18, the same as the normal lettuce (FIG. 6).

analyzed by PCR-RFLP, i.e. by digesting the PCR amplification products with restriction enzymes. That is, the PCR amplification product is digested by the restriction enzyme and based on the difference in the digestion pattern. Furthermore, the chloroplast gene rbcL was analyzed by PCR-RFLP. FIG. 9 is a photograph of electrophoresis resulting from the PCR and PCR-RFLP experiments (symbols in FIG. 9: M: molecular weight marker, S: IB5, L: Tell me, 1 to 14: 14 individuals at BC3 generation of the cytoplasmic male sterile lettuce (1216-2-T1-1 to 14)). The results are also summarized in Table 5.

TABLE 5

Analysis of cytoplasm in the progeny at BC3 generation of the cytoplasmic male sterile lettuce "1216-2" by PCR and PCR-RFLP methods

| Name of variety or line | Male sterility | Mitochondrial genes | | | | | | Chloroplast |
| --- | --- | --- | --- | --- | --- | --- | --- | --- |
| | | atp6 | coxII | cob | rps3 | trnN-trnY | trnS-trnP | gene rbcL |
| IB5 | Sterile | Sun | Sun | Sun | Sun | Sun | Sun | Sun |
| Tell Me | Fertile | Let | Let | Let | Let | Let | Let | Let |
| 1216-2-T1-1 | Sterile | Sun | Let | Let | Let | Let | Let | Let |
| 1216-2-T1-2 | Sterile | Sun | Let | Let | Let | Let | Let | Let |
| 1216-2-T1-3 | Sterile | Sun | Let | Let | Let | Let | Let | Let |
| 1216-2-T1-4 | Sterile | Sun | Let | Let | Let | Let | Let | Let |
| 1216-2-T1-5 | Sterile | Sun | Let | Let | Let | Let | Let | Let |
| 1216-2-T1-6 | Sterile | Sun | Let | Let | Let | Let | Let | Let |
| 1216-2-T1-7 | Sterile | Sun | Let | Let | Let | Let | Let | Let |
| 1216-2-T1-8 | Sterile | Sun | Let | Let | Let | Let | Let | Let |
| 1216-2-T1-9 | Sterile | Sun | Let | Let | Let | Let | Let | Let |
| 1216-2-T1-10 | Sterile | Sun | Let | Let | Let | Let | Let | Let |
| 1216-2-T1-11 | Sterile | Sun | Let | Let | Let | Let | Let | Let |
| 1216-2-T1-12 | Sterile | Sun | Let | Let | Let | Let | Let | Let |
| 1216-2-T1-13 | Sterile | Sun | Let | Let | Let | Let | Let | Let |
| 1216-2-T1-14 | Sterile | Sun | Let | Let | Let | Let | Let | Let |

Sun: Sunflower type,
Let: Lettuce type

Figure 7:
FIG. 7 shows that the cytoplasmic male sterile lettuce can produce the progeny seed when crossed with pollen of a male fertile lettuce.

When the selected cytoplasmic male sterile line "1216-2" was crossed with pollen of lettuce with normal cytoplasm, it fruited and produced seed normally as shown in FIG. 7. This confirmed that female fertility was maintained in the line.

Moreover, when "1216-2" was crossed with a male fertile lettuce, all the progeny plants exhibited male sterility. This confirmed that the male sterility was caused in cytoplasm, and transmitted by cytoplasmic inheritance.

FIG. 8 shows the result of PCR with the primers specific for the sunflower mitochondrial gene orf873, to test 14 individuals at BC3 generation after the second backcrossing of "1216-2" to "Tell me" (symbols in FIG. 8: M: molecular weight marker, S: 1B5, L: Tell me, 1 to 14: 14 individuals at BC3 generation of the cytoplasmic male sterile lettuce (1216-2-T1-1 to 14)). All individuals had orf873. This result demonstrated that the sunflower mitochondrial gene was transmitted in a stable fashion.

Figure 10:
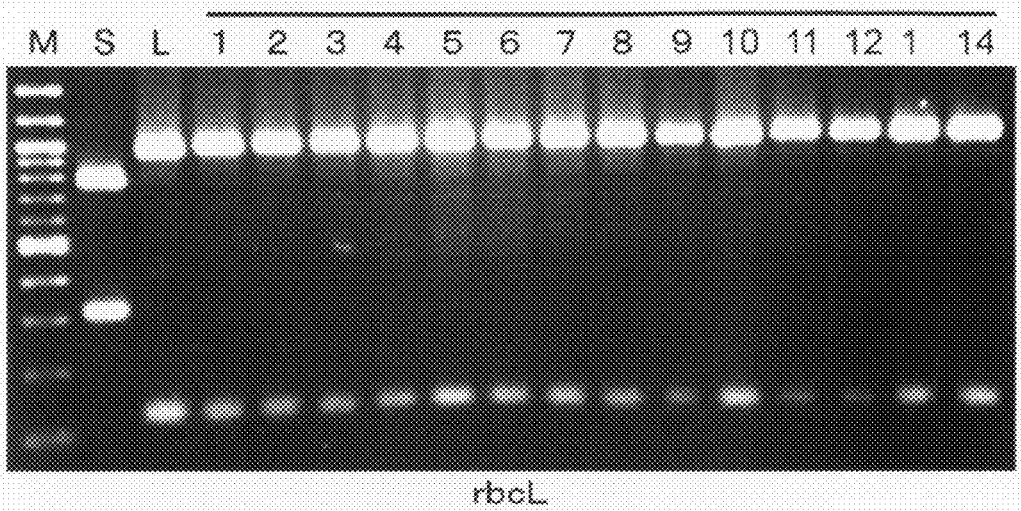
FIG. 10 is a photograph of electrophoresis showing the PCR-RFLP pattern, in which DNA was extracted from 14 individuals at BC3 generation of the cytoplasmic male sterile lettuce, PCR was performed using the DNA templates and the primers specific for the chloroplast gene rbcL, and the PCR amplification products were cut with TaqI.
Figure 11:
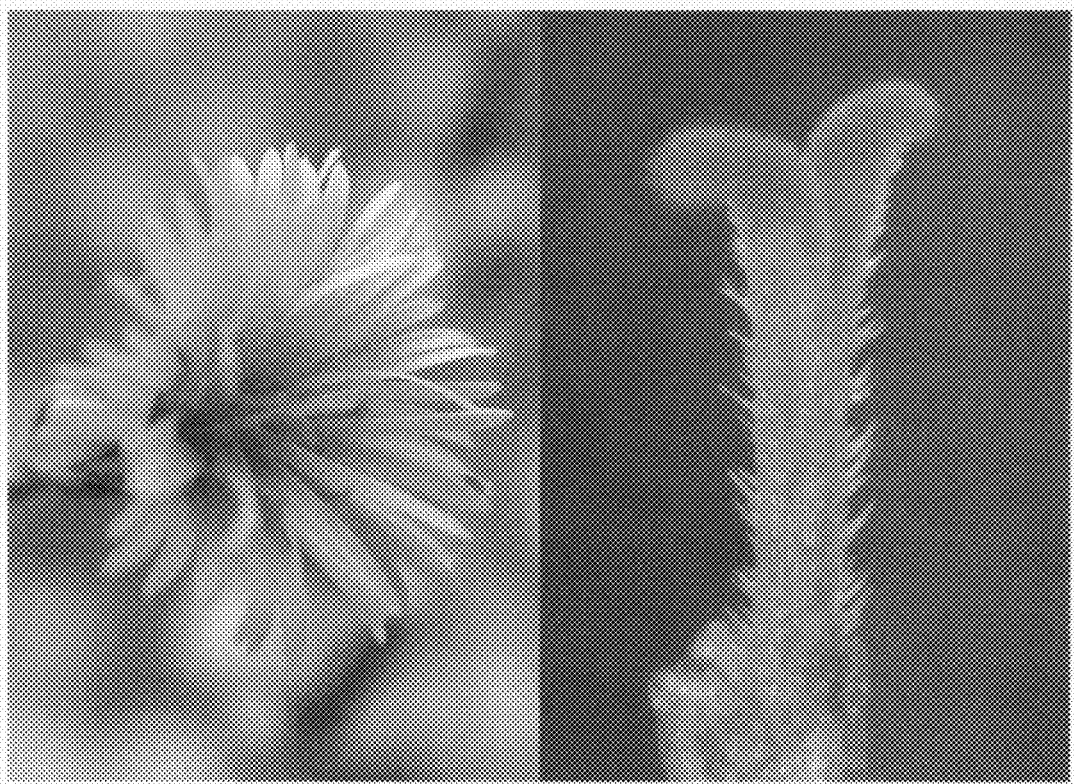
FIG. 11 shows the morphology of flower organ and pistil of an F1 plant of the cytoplasmic male sterile lettuce "12 16-2-T1"×"Tell me"
Figure 12:
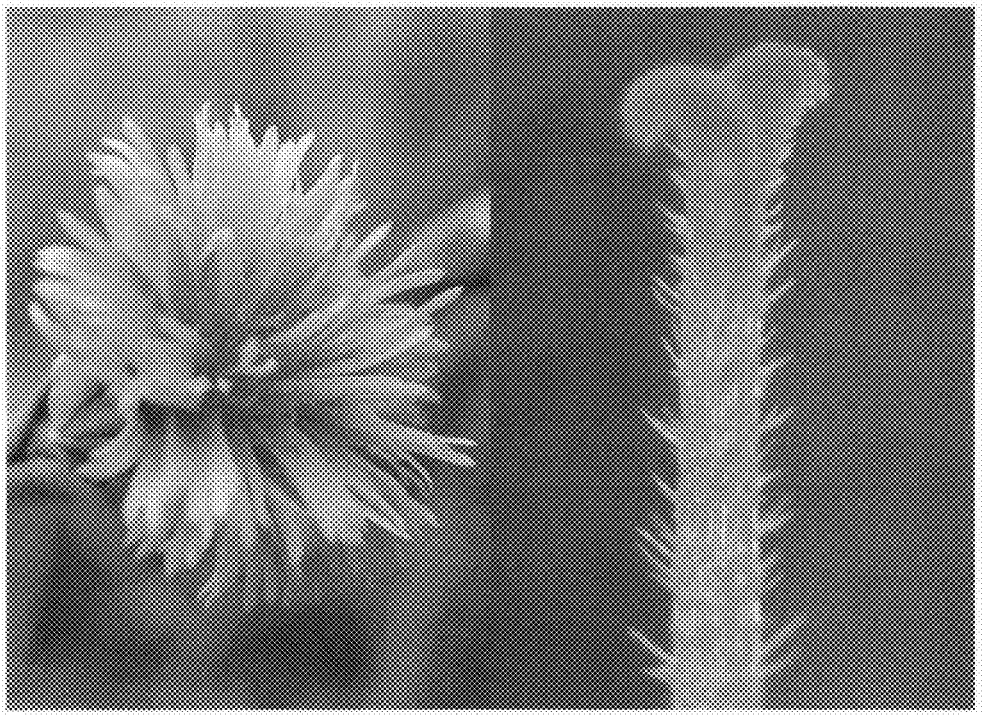
FIG. 12 shows the morphology of flower organ and pistil of an F1 plant of the cytoplasmic male sterile lettuce "12 16-2-T1"×"Steady"
Figure 13:
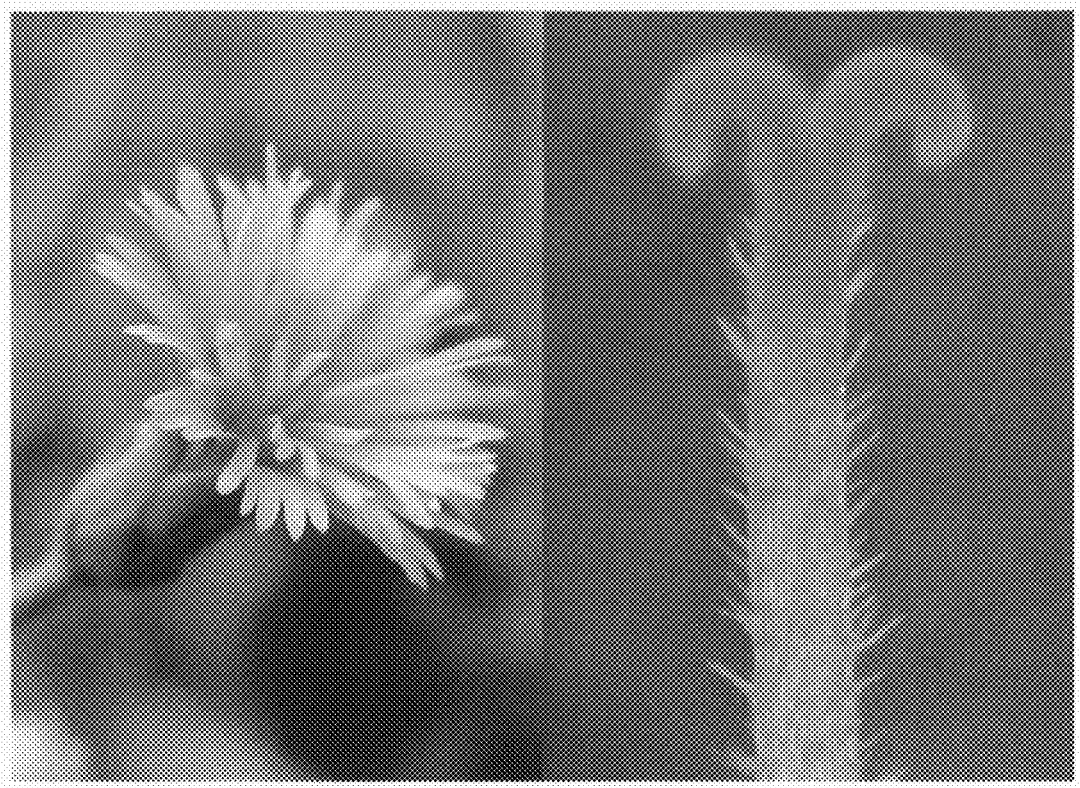
FIG. 13 shows the morphology of flower organ and pistil of an F1 plant of the cytoplasmic male sterile lettuce "12 16-2-T1"×"Logic"
Figure 14:
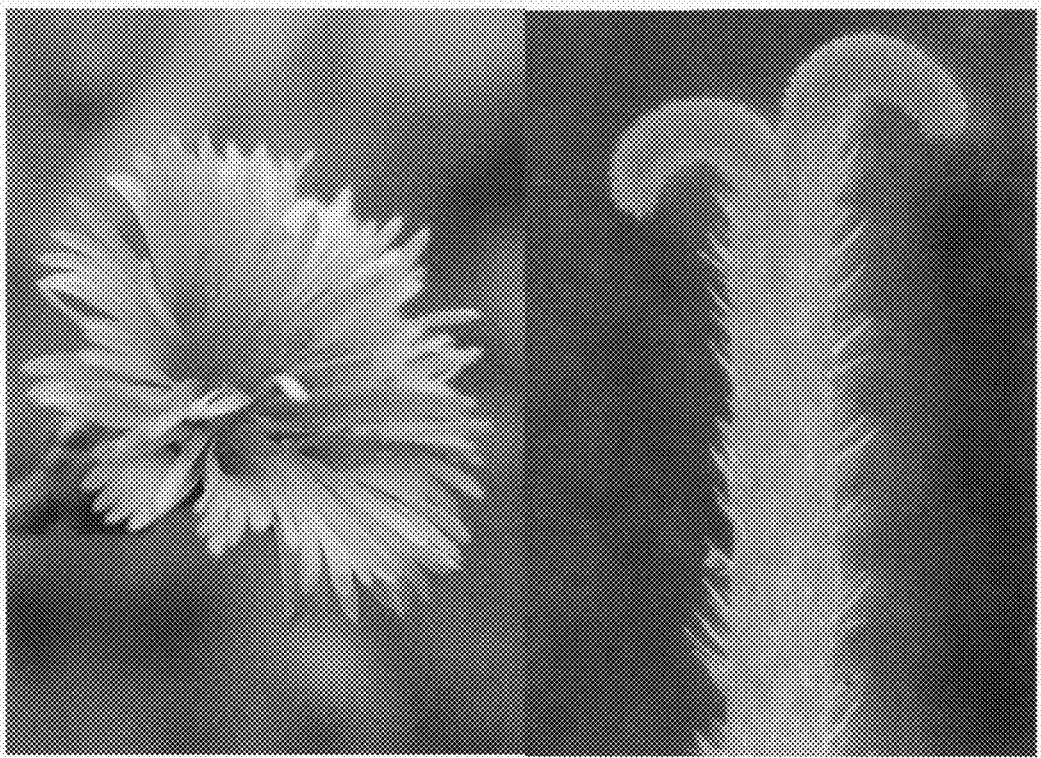
FIG. 14 shows the morphology of flower organ and pistil of an F1 plant of the cytoplasmic male sterile lettuce "12 16-2-T1"×"Miya"

Moreover, the primers listed in Table 3 were designed based on the nucleic acid sequence information of mitochondrial genes in sunflower and lettuce, publicly available in the art (Gene Bank Accession Nos. X82387, X62341, X98362, AF319170, X73425, and X87209), and other mitochondrial genes were analyzed using the PCR and PCR-RFLP methods. The mitochondrial gene rps3, the intergenic region between trnN and trnY (hereinafter, referred to as trnN-trnY), and the intergenic region between trnS and trnP (hereinafter, referred to as trnS-trnP) were analyzed by distinguishing the genotypes from the difference of the PCR amplification products in size, and the mitochondrial genes atp6, cox II, and cob were This result indicated that the mitochondrial gene atp6 appeared in sunflower type, but other mitochondrial genes analyzed appeared in lettuce type. FIG. 10 is a photograph of electrophoresis showing the result of PCR-RFLP, in which DNA was extracted from 14 individuals at BC3 generation of the cytoplasmic male sterile lettuce, PCR was performed using the DNA templates and the primers specific for the chloroplast gene rbcL, and the PCR amplification products were further digested with a restriction enzyme (symbols in FIG. 10: M: molecular weight marker, S: 1B5, L: Tell me, 1 to 14: 14 individuals at BC3 generation of the cytoplasmic male sterile lettuce (1216-2-T1-1 to 14)). The result of PCR-RFLP shown in FIG. 10 demonstrated that the chloroplast gene rbcL also appeared in lettuce type in all individuals. Thus, it was found that only a portion of the sunflower mitochondrial genes were incorporated into the cytoplasmic male sterile lettuce produced in the present invention, and chloroplasts were derived from lettuce. Furthermore, all 14 individuals of the progeny used for the testing appeared in the same band pattern. This indicated that the mitochondrial genome was stable in the progeny. However, the results shown in FIGS. 9, 10, and Table 5 are just exemplary results of the analysis on individuals that express cytoplasmic male sterility, and the band patterns in cytoplasmic male sterile lettuce are not necessarily in the same pattern.

The above results demonstrated that a cytoplasmic male sterile lettuce can be produced by introducing a portion of sunflower mitochondrial DNA by asymmetric protoplast fusion. Based on the results of analysis of cytoplasm so far, it was considered that male sterility was caused by the induction of recombination of the mitochondrial gene(s) that are responsible for male sterility, or rearrangement of the mitochondrial genome.

Thus, the cybrid lettuce created by the present invention was found to be a cytoplasmic male sterile lettuce with an elaborate recombination of the mitochondrial genome, which has the trait of cytoplasmic male sterility due to the alteration of mitochondrial genome, and at the same time, has the mitochondrial genome highly compatible with the nuclear genome of lettuce.

(7) Use of Cytoplasmic Male Sterile Plants and the Production of F1 Seed

The produced cytoplasmic male sterile lettuce, for example "1216-2-T1", which is the progeny of crossing "1216-2" with "Tell me", was crossed with 5 commercially available true-breeding varieties "Tell me" (Sakata Seed Corporation), "Steady" (Tsuruta Seed), "Logic" (The Yokohama Nursery Co., Ltd.), "Miya" (Sumika Agrotech Co., Ltd.), and "V lettuce" (Kaneko Seeds) as a pollen parent, and the F1 seed was harvested.

Figure 15:
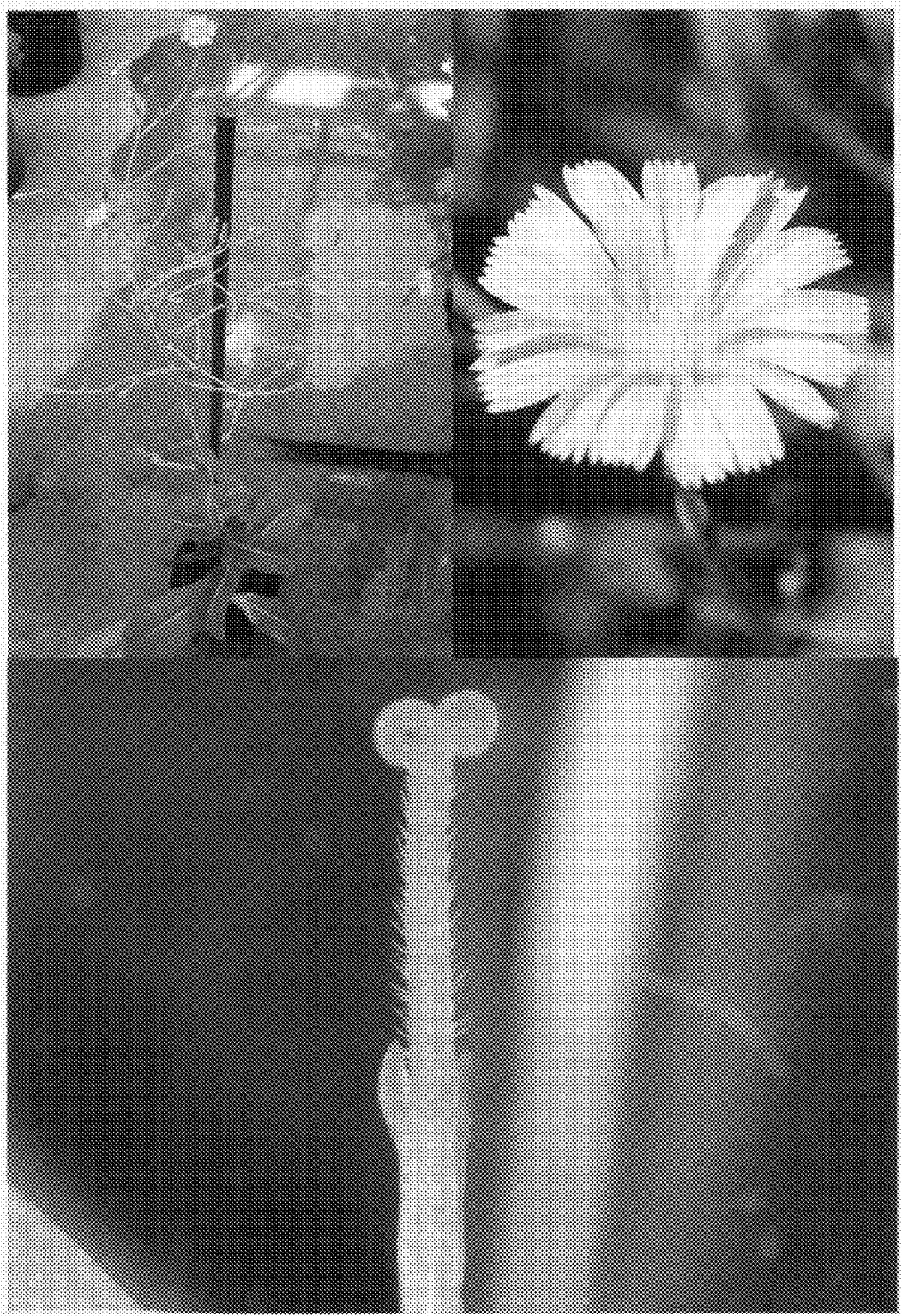
FIG. 15 shows the morphology of plant, flower organ and pistil of an F1 plant of the cytoplasmic male sterile lettuce "12 16-2-T1" ×the lettuce wild species *L. serriola*.

After seeding the F1 seed on a plug tray and raising the seedlings, they were planted in No. 10 pots and grown as usual in a greenhouse, and then investigated for their properties. 3 strains for each line or variety were tested. All lines and varieties grew normally. Male sterility of each line or variety was investigated with 10 flowers for each strain. A stereoscopic microscope was used for the detailed observations. The petal color and flower organ shape were observed one by one when they were blooming, and the presence of self-pollinated seed was also examined after blooming. The results of the examinations were shown in Table 6. All of the individual F1 lines including "1216-2-T1" and the above 5 true breeding varieties exhibited 100% male sterility. Moreover, as shown in FIGS. 11 to 14, adhesion of pollen on the pistil by self-pollination was not observed at all, also in the cases of crossing with the lettuce varieties other than "Tell me", and there was no sign of pollen in the anthers. Furthermore, as shown in FIG. 15, adhesion of pollen on the pistil by self-pollination was not observed in the hybrid progeny developed from crossing with pollen of the lettuce wild species L. serriola, and there was no sign of pollen in the anthers either.

This result demonstrated that male sterility was maintained without producing any pollen even when the nuclear genes were changed into a genotype other than 'Tell me', and confirmed that its male sterility is caused in cytoplasm. Thus, the cybrid plants produced in accordance with the present invention were demonstrated to show stable cytoplasmic male sterility.

Furthermore, female fertility of the cytoplasmic male sterile lines, which do not produce pollen, was investigated by crossing with pollen of the same variety used for producing F1. 10 flowers were examined for a strain, and the lines or variety with the ability to produce 10 or more seeds per flower were scored as "yes" in female fertility. As shown in Table 6, all cytoplasmic male sterile lines had female fertility regardless of the difference in genotype. This confirmed that the cytoplasmic male sterile lettuce produced in accordance with the present invention can be used for the efficient F1 seed production.

TABLE 6

Analysis of the properties in the flower organ of F1 plants between lettuce test varieties and cytoplasmic male sterile lettuce at BC3 generation "1216-2-T1"

| Line or variety | Rate of pollen production (%) | Color of petal | Abnormality in flower organ | Seed from self-pollination | Female fertility |
| --- | --- | --- | --- | --- | --- |
| Tell Me | 100 | Yellow | No | Yes | Yes |
| Steady | 100 | Yellow | No | Yes | Yes |
| Logic | 100 | Yellow | No | Yes | Yes |
| Miya | 100 | Yellow | No | Yes | Yes |
| V lettuce | 100 | Yellow | No | Yes | Yes |

TABLE 6-continued

Analysis of the properties in the flower organ of F1 plants between lettuce test varieties and cytoplasmic male sterile lettuce at BC3 generation "1216-2-T1"

| Line or variety | Rate of pollen production (%) | Color of petal | Abnormality in flower organ | Seed from self-pollination | Female fertility |
| --- | --- | --- | --- | --- | --- |
| 1216-2-T1X Tell Me | 0 | Yellow | No | No | Yes |
| 1216-2-T1X Steady | 0 | Yellow | No | No | Yes |
| 1216-2-T1X Logic | 0 | Yellow | No | No | Yes |
| 1216-2-T1X Miya | 0 | Yellow | No | No | Yes |
| 1216-2-T1XV lettuce | 0 | Yellow | No | No | Yes |

The rate of pollen production: the number of flowers producing pollen/the total number of examined flowers The seed of "1216-2-T1", the progeny from the crossing between "1216-2" and "Tell me" was deposited, under terms of the Budapest Treaty, with the International Patent Organism Depositary at National Institute of Advanced Industrial Science and Technology (Chuo 6, 1-1-1 Higashi, Tsukuba, Ibaraki, Japan) on 29 Sep. 2005 (Identification reference given by the depositor SSC-LET-05-001 and Accession number FERM BP-10421).

The seed of "1216-2-T1", the progeny from the crossing between "1216-2" and "Tell me" was deposited to International Patent Organism Depositary at National Institute of Advanced Industrial Science and Technology (Chuo 6, 1-1-1 Higashi, Tsukuba, Ibaraki, Japan) on 29 Sep. 2005 (Identification reference given by the depositor SSC-LET-05-001 and Accession number FERM BP-10421).

EXAMPLE 2

Cytoplasmic male sterile cybrid plant "50125-3" was produced using "1216-2-T1" as donor material to provide cytoplasm and performing asymmetric protoplast fusion with "V lettuce" (Kaneko Seeds). In the flower of "50125-3", no pollen grains adhered to the pistil were observed, and also no pollen grains were observed in the anther of the flower. Furthermore, no obvious differences were observed in the shape of the flower organ and the like, in comparison with "V lettuce". When the selected cytoplasmic male sterile line "50125-3" was crossed with pollen of a lettuce with normal cytoplasm, it fruited and produced seed normally. This confirmed that female fertility was maintained in the line. In addition, when "50125-3" was crossed with pollen of a male fertile lettuce, all progeny plants were male sterile. This confirmed that the male sterility was caused by cytoplasm and was cytoplasmic inheritance.

Table 7 shows the PCR and PCR-RFLP analysis results of mitochondrial genes of ten individuals "50125-3-V1-1 to −10" that are progenies obtained by crossing "50125-3" with "V lettuce". It was observed, for example, that both sunflower-type and lettuce-type atp6 genes were maintained in "50125-3-V1-1 to −10", as a difference compared to "1216-2-T1" used as donor material to provide cytoplasm.

However, the results shown in FIG. 7 are exemplary results of the analysis on individuals that express cytoplasmic male sterility, and the band patterns in cytoplasmic male sterile lettuce are not necessarily in the same pattern.

The seed of "50125-3-V1", the progeny from the crossing between "50125-3" and "V lettuce" was deposited, under terms of the Budapest Treaty, with the International Patent Organism Depositary at National Institute of Advanced Industrial Science and Technology (Chuo 6, 1-1-1 Higashi, Tsukuba, Ibaraki, Japan) on 31 Jul. 2006 (Identification reference given by the depositor SSC-LET-06-001 and Accession number FERM BP-10647).

TABLE 7

Analysis of cytoplasm in the progeny at BC2 generation of the cytoplasmic male sterile lettuce "50125-3-V1" by PCR and PCR-RFLP methods

| Name of variety or line | Male sterility | orf873 | atp6 | coxII | cob | rps3 | trnN-trnY | trnS-trnP | gene rbcL |
|---|---|---|---|---|---|---|---|---|---|
| IB5 | Sterile | + | Sun | Sun | Sun | Sun | Sun | Sun | Sun |
| V lettuce | Fertile | − | Let | Let | Let | Let | Let | Let | Let |
| 50125-3-V1-1 | Sterile | + | Sun + Let | Let | Let | Let | Let | Let | Let |
| 50125-3-V1-2 | Sterile | + | Sun + Let | Let | Let | Let | Let | Let | Let |
| 50125-3-V1-3 | Sterile | + | Sun + Let | Let | Let | Let | Let | Let | Let |
| 50125-3-V1-4 | Sterile | + | Sun + Let | Let | Let | Let | Let | Let | Let |
| 50125-3-V1-5 | Sterile | + | Sun + Let | Let | Let | Let | Let | Let | Let |
| 50125-3-V1-6 | Sterile | + | Sun + Let | Let | Let | Let | Let | Let | Let |
| 50125-3-V1-7 | Sterile | + | Sun + Let | Let | Let | Let | Let | Let | Let |
| 50125-3-V1-8 | Sterile | + | Sun + Let | Let | Let | Let | Let | Let | Let |
| 50125-3-V1-9 | Sterile | + | Sun + Let | Let | Let | Let | Let | Let | Let |
| 50125-3-V1-10 | Sterile | + | Sun + Let | Let | Let | Let | Let | Let | Let |

+: present,
−: absent
Sun: Sunflower type,
Let: Lettuce type

INDUSTRIAL APPLICABILITY

The present invention provides a cybrid lettuce that has cytoplasm derived from sunflower. When the cybrid lettuce according to the present invention is a cytoplasmic male sterile lettuce, efficient and high purity production of F1 seed can be achieved by using this lettuce as a seed parent, in contrast to the commercial F1 seed production using a genetic male sterile plant.

All publications, patents, and patent applications cited herein are hereby incorporated by reference.

---

The invention claimed is:

1. A cybrid plant of the genus *Lactuca*, a progeny thereof, or a part thereof, comprising, in cytoplasm thereof, a gene derived from mitochondria of a plant of the genus *Helianthus* and being cytoplasmic male sterile.

2. The cybrid plant of the genus *Lactuca*, or the progeny thereof, or the part thereof according to claim 1, wherein the plant of the genus *Helianthus* is *H. annuus* L. or a cytoplasm substitution line of *H. annuus* L. with cytoplasm from *H. petiolaris, H. argophyllus, H. debilis, H. decapetalus, H. giganteus, H. rigidus, H. salicifolius, H. anomalus, H. bolanderi, H. exilis, H. maximiliani, H. neglectus, H. praecox* or *H. tuberosus*.

3. The cybrid plant of the genus *Lactuca*, or the progeny thereof, or the part thereof according to claim 1, wherein the cybrid plant of the genus *Lactuca* is derived from *Lactuca sativa* L., *L. serriola, L. aculeate, L. scarioloides, L. azerbaijanica, L. georgica, L. dregeana, L. altaica, L. saligna, L. virosa, L. tatarica, L. indica* or *L. debilis* or the interspecific hybrid plant thereof.

4. The cybrid plant of the genus *Lactuca*, or the progeny thereof, or the part thereof according to claim 1, wherein the gene derived from mitochondria of a plant of the genus *Helianthus* is a male sterile gene.

5. The cybrid plant of the genus *Lactuca*, or the progeny thereof, or the part thereof according to claim 1, produced by a method characterized by comprising: fusing protoplasts from a plant of the genus *Helianthus* with protoplasts from a plant of the genus *Lactuca*; culturing one or more of the fused cells; and regenerating a plant of the genus *Lactuca* from cells cultured from one or more of the fused cells.

6. The part of the cybrid plant of the genus *Lactuca* or the progeny thereof according to claim 1, wherein the part comprises a cell or cytoplasm of the plant.

7. A microcallus comprising cells of the cybrid plant of the genus *Lactuca* according to claim 1.

8. A method for producing first filial generation seed, comprising:

crossing, as a seed parent, the cybrid plant of the genus *Lactuca* according to claim 1, or the progeny thereof, with, as a pollen parent, a plant of the genus *Lactuca* that is crossable with the cybrid plant; and harvesting first filial generation seed produced by the seed parent after the crossing.

9. A seed of the cybrid plant of the genus *Lactuca* that has been deposited under Accession No. FERM BP-10421, a cybrid plant of the genus *Lactuca* grown from the seed, or the progeny thereof, or a part thereof.

10. The part of the cybrid plant of the genus *Lactuca* or the progeny thereof according to claim 9, wherein the part comprises a cell or cytoplasm of the plant.

11. A method for producing first filial generation seed, comprising:

crossing, as a seed parent, the cybrid plant of the genus *Lactuca* according to claim 9, or the progeny thereof, with, as a pollen parent, a plant of the genus *Lactuca* that is crossable with the cybrid plant; and harvesting first filial generation seed produced by the seed parent after the crossing.

12. A seed of the cybrid plant of the genus Lactuca that has been deposited under Accession No. FERM BP-10647, a cybrid plant of the genus *Lactuca* grown from the seed, or the progeny thereof, or a part thereof.

13. The part of the cybrid plant of the genus *Lactuca* or the progeny thereof according to claim 12, wherein the part comprises a cell or cytoplasm of the plant.

14. A method for producing first filial generation seed, comprising:

crossing, as a seed parent, the cybrid plant of the genus *Lactuca* according to claim 12, or the progeny thereof, with, as a pollen parent, a plant of the genus *Lactuca* that is crossable with the cybrid plant; and harvesting first filial generation seed produced by the seed parent after the crossing.

* * * * *